United States Patent
Chan et al.

(10) Patent No.: US 12,419,883 B2
(45) Date of Patent: Sep. 23, 2025

(54) LIQUID FORMULATIONS OF INDACATEROL

(71) Applicant: AeroRx Therapeutics, Inc., La Jolla, CA (US)

(72) Inventors: John Chan, San Francisco, CA (US); Keith Try Ung, San Carlos, CA (US); Mei-Chang Kuo, Palo Alto, CA (US); John Nigel Pritchard, Leicestershire (GB)

(73) Assignee: AERORX THERAPEUTICS, INC., La Jolla, CA (US)

( * ) Notice: Subject to any disclaimer, the term of this patent is extended or adjusted under 35 U.S.C. 154(b) by 67 days.

(21) Appl. No.: 18/503,992

(22) Filed: Nov. 7, 2023

(65) Prior Publication Data
US 2024/0091216 A1    Mar. 21, 2024

Related U.S. Application Data

(62) Division of application No. 17/449,412, filed on Sep. 29, 2021, now Pat. No. 11,844,793.
(Continued)

(51) Int. Cl.
*A61K 31/4704*    (2006.01)
*A61K 9/00*    (2006.01)
(Continued)

(52) U.S. Cl.
CPC ........ *A61K 31/4704* (2013.01); *A61K 9/0078* (2013.01); *A61K 9/08* (2013.01);
(Continued)

(58) Field of Classification Search
CPC ........... A61P 11/00; A61P 11/06; A61P 29/00; A61P 11/02; A61P 13/12; A61P 19/02; A61P 25/00; A61P 25/28; A61P 3/10; A61P 35/00; A61P 37/02; A61P 43/00; A61P 9/10; A61P 17/00; A61P 19/00;
(Continued)

(56) References Cited

U.S. PATENT DOCUMENTS

| 6,878,721 | B1 | 4/2005 | Cuenoud et al. |
| 7,820,694 | B2 | 10/2010 | Cuenoud et al. |

(Continued)

FOREIGN PATENT DOCUMENTS

| CN | 103784449 A | 5/2014 |
| EP | 3157522 B1 | 9/2019 |

(Continued)

OTHER PUBLICATIONS

International Preliminary Report on Patentability, issued Mar. 28, 2023, for PCT Application No. PCT/US2021/71646, filed Sep. 2021, 9 pages.

(Continued)

*Primary Examiner* — Savitha M Rao
(74) *Attorney, Agent, or Firm* — MORRISON & FOERSTER LLP

(57) ABSTRACT

Aqueous formulations of indacaterol are disclosed. The formulations may find use in the treatment of respiratory disorders, inflammatory disorders, or obstructive airway diseases. Methods of using the formulations and kits comprising the formulations are also encompassed by the disclosure.

39 Claims, 10 Drawing Sheets

Related U.S. Application Data

Figure 1:
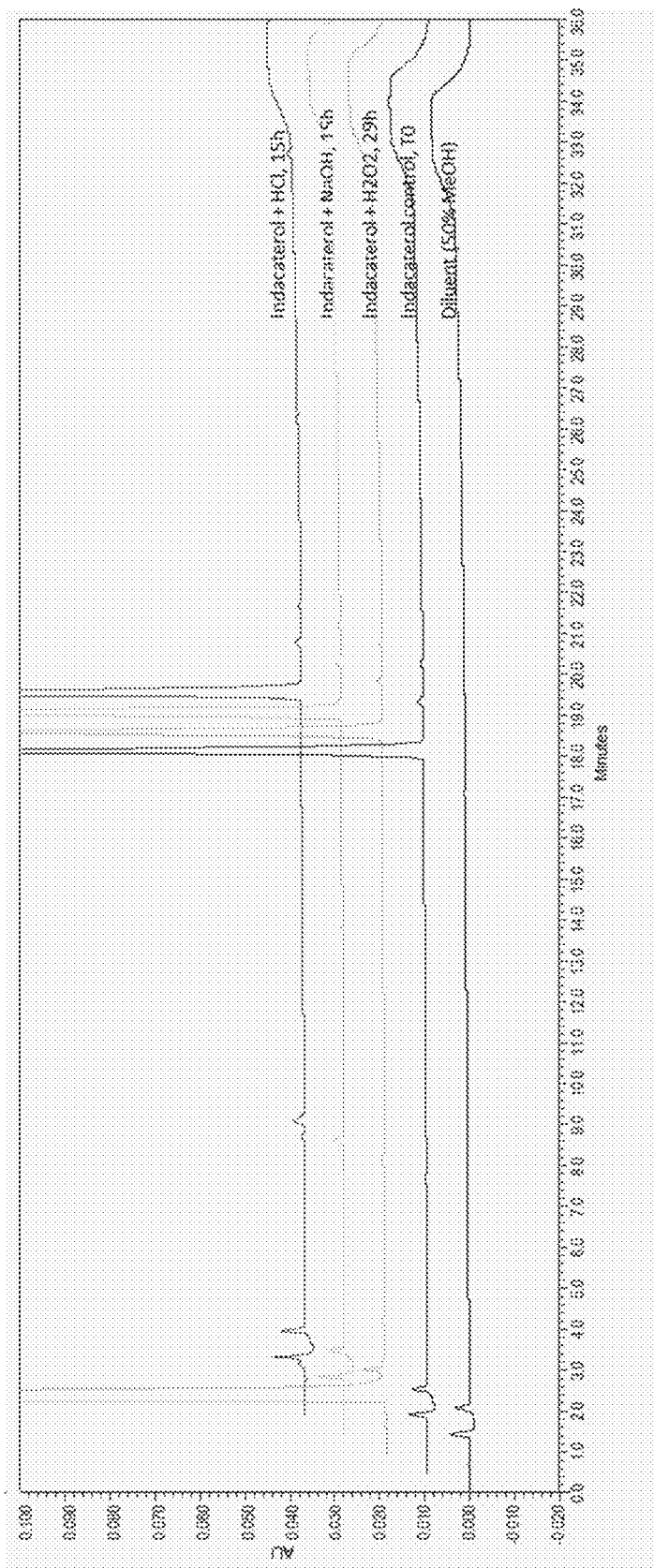

(60) Provisional application No. 63/085,057, filed on Sep. 29, 2020.

(51) Int. Cl.
| | | |
|---|---|---|
| *A61K 9/08* | (2006.01) | |
| *A61K 9/12* | (2006.01) | |
| *A61K 31/40* | (2006.01) | |
| *A61K 31/5386* | (2006.01) | |
| *A61K 31/58* | (2006.01) | |
| *A61K 47/10* | (2017.01) | |
| *A61K 47/26* | (2006.01) | |
| *A61K 47/69* | (2017.01) | |
| *A61P 11/00* | (2006.01) | |

(52) U.S. Cl.
CPC ............... *A61K 9/12* (2013.01); *A61K 31/40* (2013.01); *A61K 31/5386* (2013.01); *A61K 31/58* (2013.01); *A61K 47/10* (2013.01); *A61K 47/26* (2013.01); *A61K 47/6951* (2017.08); *A61P 11/00* (2018.01)

(58) Field of Classification Search
CPC .......... A61P 31/00; A61P 31/12; A61P 37/00; A61P 9/00; A61P 11/16; A61P 17/04; A61P 17/06; A61P 19/10; A61P 31/18; A61P 37/06; A61P 37/08; C07D 471/04; A61K 31/66; A61K 2039/5158; A61K 2039/55522; A61K 31/40; A61K 31/4704; A61K 31/5386; A61K 31/58; A61K 38/2221; A61K 39/395; A61K 47/10; A61K 47/26; A61K 47/6951; A61K 9/0075; A61K 9/0078; A61K 9/08; A61K 9/12; A61K 9/1617; A61K 9/1682; A61K 9/1688; A61M 11/001; A61M 15/0021; A61M 15/0028; A61M 15/0035; A61M 15/0041; A61M 15/0045; A61M 15/0093; A61M 2202/0007; A61M 2202/064
See application file for complete search history.

(56) References Cited

U.S. PATENT DOCUMENTS

| | | |
|---|---|---|
| 8,067,437 B2 | 11/2011 | Cuenoud et al. |
| 8,283,362 B2 | 10/2012 | Cuenoud et al. |
| 8,658,673 B2 | 2/2014 | Cuenoud et al. |
| 9,220,708 B2 | 12/2015 | Ruecroft et al. |
| 9,474,747 B2 | 10/2016 | Albrecht et al. |
| 10,179,139 B2 | 1/2019 | Malhotra et al. |
| 11,844,793 B2 | 12/2023 | Chan |
| 2007/0020299 A1 | 1/2007 | Pipkin et al. |
| 2009/0130026 A1 | 5/2009 | Lewis et al. |
| 2009/0298802 A1 | 12/2009 | Sequeira et al. |
| 2011/0023876 A1 | 2/2011 | Vehring |
| 2014/0147393 A1 | 5/2014 | Malhorta et al. |
| 2014/0308214 A1 | 10/2014 | Malhotra et al. |
| 2016/0326118 A1 | 11/2016 | Ravi |
| 2017/0065518 A1 | 3/2017 | Lewis et al. |
| 2017/0202787 A1 | 7/2017 | Gerhart et al. |
| 2017/0296510 A1 | 10/2017 | Burns et al. |
| 2018/0117026 A1 | 5/2018 | Dewitt et al. |
| 2018/0133151 A1 | 5/2018 | Dhuppad et al. |
| 2019/0030268 A1 | 1/2019 | Huang |
| 2019/0262329 A1 | 8/2019 | Albrecht et al. |
| 2019/0374532 A1* | 12/2019 | Corr ..................... A61K 9/008 |
| 2020/0163955 A1 | 5/2020 | Dhuppad et al. |
| 2020/0215051 A1 | 7/2020 | Kulkarni et al. |
| 2020/0375945 A1 | 12/2020 | Huang et al. |
| 2021/0386730 A1 | 12/2021 | Huang et al. |
| 2022/0096456 A1 | 3/2022 | Chan |
| 2025/0177372 A1 | 6/2025 | Chan et al. |

FOREIGN PATENT DOCUMENTS

| | | |
|---|---|---|
| WO | 2000075114 A1 | 12/2000 |
| WO | 2006105401 A2 | 10/2006 |
| WO | 2006105401 A3 | 6/2007 |
| WO | 2007121913 A2 | 11/2007 |
| WO | 2007121913 A3 | 3/2008 |
| WO | 2008102128 A2 | 8/2008 |
| WO | 2008102128 A3 | 1/2009 |
| WO | 2012007729 A2 | 1/2012 |
| WO | 2012049444 A1 | 4/2012 |
| WO | 2012007729 A3 | 5/2012 |
| WO | 2015001880 A1 | 1/2015 |
| WO | 2016046553 A1 | 3/2016 |
| WO | 2016153948 A1 | 9/2016 |
| WO | 2016178019 A1 | 11/2016 |
| WO | 2019142214 A1 | 7/2019 |
| WO | 2020019952 A1 | 1/2020 |
| WO | 2020105012 A1 | 5/2020 |
| WO | 2020141472 A1 | 7/2020 |
| WO | 2020217116 A2 | 10/2020 |
| WO | 2020247376 A1 | 12/2020 |
| WO | 2021068961 A1 | 4/2021 |
| WO | 2023192445 A1 | 10/2023 |
| WO | 2024033626 A1 | 2/2024 |
| WO | 2024206662 A1 | 10/2024 |

OTHER PUBLICATIONS

International Search Report and Written Opinion, mailed Feb. 18, 2022, for PCT Application No. PCT/US2021/71646, filed Sep. 2021, 13 pages.

International Search Report and Written Opinion, mailed Jul. 13, 2023, for PCT Application No. PCT/US2023/016847, filed Sep. 2021, 8 pages.

Invitation to Pay Additional Fees, mailed Dec. 2, 2021, for PCT Application No. PCT/US2021/71646, filed Sep. 2021, 2 pages.

Non-Final Office Action, mailed Jun. 1, 2023, for U.S. Appl. No. 17/449,412, filed Sep. 29, 2021, 16 pages.

Product Information (Oct. 3, 2022). "Item No. 20070—Indacaterol," Cayman Chemical, 1 page.

Tiwari, G. et al. (Apr.-Jun. 2010). "Cyclodextrins in Delivery Systems: Applications," Journal of Pharmacy & Bioallied Sciences 2(2):72-79, 17 pages.

International Preliminary Report on Patentability, issued Sep. 24, 2024, for PCT Application No. PCT/US2023/016847, filed Mar. 30, 2023, 7 pages.

International Search Report and Written Opinion, mailed Jul. 10, 2024, for PCT Application No. PCT/US2024/022018, filed Mar. 28, 2024, 8 pages.

* cited by examiner

LIQUID FORMULATIONS OF INDACATEROL

CROSS-REFERENCE TO RELATED APPLICATIONS

This application is a divisional application of U.S. patent application Ser. No. 17/449,412, filed on Sep. 29, 2021, which claims priority to and the benefit of U.S. Provisional Application No. 63/085,057 filed on Sep. 29, 2020, the disclosures of which are hereby incorporated herein by reference in their entireties for all purposes.

BACKGROUND OF THE INVENTION

Currently marketed inhaled dosage forms for symptomatic treatment of COPD typically contain an active pharmaceutical agent (API) that is a long acting beta agonist (LABA), long acting muscarinic antagonist (LAMA), and/or an inhaled corticosteroid (ICS). These APIs, either individually or in combination, are typically administered to the lung via dry powder inhalers (DPIs), metered dose pressurized inhalers (pMDIs) or soft mist inhalers (SMIs). Although these inhalation drug delivery devices are adequate for most patients, a segment of the COPD population (e.g. the elderly) may have difficulties effectively using these devices, thus leading to inadequate treatment for a particularly vulnerable patient population. This may be due to challenges generating sufficient inspiratory effort for DPIs or having insufficient device actuation/inhalation coordination for MDIs/SMIs. Alternative compositions that can be more easily administered are desired, particularly for patient populations that cannot effectively take advantage of currently available treatments.

BRIEF SUMMARY OF THE INVENTION

The present disclosure relates to liquid compositions comprising an inhalable active pharmaceutical agent. The liquid compositions may find use in treatment methods for which the APIs may be used, and may find particular benefits in patient populations for whom existing APIs delivered via DPIs, pMDIs or SMIs are inadequate. The liquid compositions may simplify delivery of the API by permitting delivery via nebulizers, thereby addressing many of the common problems associated with currently available treatments, such as coughing, coordination, and high inspiratory effort. Particularly, administering inhalable pharmaceuticals via nebulizers allows a patient to receive an adequate dose using low tidal breathing, improving lung delivery and minimizing throat deposition. Normally, cough is associated with high throat deposition which is considered a side effect from the product.

In particular, provided are aqueous compositions comprising indacaterol or a pharmaceutically acceptable salt thereof. The compositions herein may be used for the treatment of respiratory diseases and disorders, such as COPD and asthma. The compositions comprising indacaterol are therefore notable in that they provide a room temperature stable aqueous solution comprising indacaterol or a pharmaceutically acceptable salt thereof and are thus amenable to delivery methods that were previously unattainable with this API. In some embodiments, the compositions comprise excipients such as a buffer, a solubilizing agent, a tonicity modifier, and a co-solvent.

In some embodiments, an aqueous composition provided herein comprises from about 20 weight percent to 99.9 weight percent water and indacaterol, or a pharmaceutically acceptable salt thereof, at a concentration of about 10 μg/mL to about 2 mg/mL. In some embodiments, the indacaterol is present as a free base. In some embodiments, the indacaterol is present as a pharmaceutically acceptable salt. In some embodiments, the indacaterol is present as indacaterol maleate.

In some embodiments, an aqueous composition comprising indacaterol or a pharmaceutically acceptable salt thereof provided herein further comprises a solubilizing agent. In some embodiments, the solubilizing agent is a complexing agent. In some embodiments, the complexing agent is a cyclodextrin. In some embodiments, the cyclodextrin is selected from the group consisting of β-CD (β-cyclodextrin), SBE-β-CD (sulfobutylether-β-cyclodextrin), HP-β-CD (hydroxypropyl-β-cyclodextrin), and γ-CD (γ-cyclodextrin). In some embodiments, the cyclodextrin is SBE-β-CD. In some embodiments, the cyclodextrin is present in an amount from about 0.1% w/v, to about 10% w/v. In some embodiments, the cyclodextrin is present from about 0.25% w/v to about 1% w/v.

In some embodiments, an aqueous composition comprising indacaterol or a pharmaceutically acceptable salt thereof provided herein further comprises one or more tonicity modifiers. In some embodiments, the one or more tonicity modifier is mannitol. In some embodiments, the one or more tonicity modifier is sodium chloride. In some embodiments, the one or more tonicity modifier is present at a concentration of about 50 mM to about 500 mM. In some embodiments, the one or more tonicity modifier is present at a concentration of about 200 mM to about 350 mM. In some embodiments, the one or more tonicity modifier is present at a concentration of about 100 mM to about 200 mM. In some embodiments, the composition comprises two or more tonicity modifiers, such as mannitol and sodium chloride, and each tonicity modifier is individually present at different concentrations.

In some embodiments, an aqueous composition comprising indacaterol or a pharmaceutically acceptable salt thereof provided herein further comprises a co-solvent. In some embodiments, the co-solvent is an alcohol. In some embodiments, the co-solvent is ethanol or ethylene glycol. In some embodiments, the co-solvent is a combination of ethanol and ethylene glycol. In some embodiments, the co-solvent is present in an amount from about 0.1% v/v to about 10% v/v. In some embodiments, the co-solvent is present in an amount from about 0.1% to about 5%, about 2%, about 1%, or about 0.5%. In some embodiments, the co-solvent is present in an amount of about 5%.

In some embodiments, an aqueous composition comprising indacaterol or a pharmaceutically acceptable salt thereof further comprises a buffer. The aqueous composition may comprise a buffer via incorporation of an applicable acid or base or salt of the foregoing. In some embodiments, the buffer comprises an anion selected from the group consisting of acetate, bromide, chloride, citrate, furoate, fumarate, maleate, malate, propionate, succinate, sulfate, tartrate, and xinafoate. In some embodiments, the buffer is prepared from a combination of citric acid and trisodium citrate or a combination of citric acid and sodium hydroxide. In some embodiments, the anion is present at a concentration from about 1 mM to about 100 mM. In some embodiments, the anion is present at a concentration from about 1 mM to about 10 mM.

In some embodiments, an aqueous composition comprising indacaterol or a pharmaceutically acceptable salt thereof provided herein has a pH from 2 to 6. In some embodiments, the aqueous composition has a pH from 3 to 5. In some embodiments, the aqueous composition has a pH from 3.5 to 4.5. In some embodiments, the aqueous composition has a pH of 4.

In some embodiments, an aqueous composition provided herein comprising indacaterol or a pharmaceutically acceptable salt thereof further comprises an additional pharmaceutical agent. In some embodiments, the additional pharmaceutical agent is a long acting muscarinic antagonist and/or an inhaled corticosteroid. In some embodiments, the long acting muscarinic antagonist is tiotropium or a pharmaceutically acceptable salt thereof. In some embodiments, the long acting muscarinic antagonist is tiotropium bromide. In some embodiments, the long acting muscarinic antagonist is glycopyrrolate or a pharmaceutically acceptable salt thereof. In some embodiments, the long acting muscarinic antagonist is glycopyrronium bromide. In some embodiments, an aqueous combination provided herein comprising indacaterol or a pharmaceutically acceptable salt thereof further comprises two additional pharmaceutical agents. In some embodiments, the additional pharmaceutical agents comprise a long acting muscarinic antagonist and an inhaled corticosteroid. In some embodiments, the long acting muscarinic antagonist is tiotropium or pharmaceutically acceptable salt thereof and the inhaled corticosteroid is mometasone or a pharmaceutically acceptable salt thereof.

In some embodiments, an aqueous composition provided herein comprising indacaterol or a pharmaceutically acceptable salt thereof further comprises a complexing agent, one or more tonicity modifiers, and a buffer. In some embodiments, the complexing agent is a cyclodextrin, the one or more tonicity modifiers is mannitol, and the buffer comprises citrate. In some embodiments, the cyclodextrin is present in an amount from about 0.25% w/v to about 1% w/v, mannitol is present at a concentration from about 100 mM to about 500 mM, and the pH is from 3 to 6. In some embodiments, the cyclodextrin is present in an amount of about 0.5% w/v, mannitol is present at a concentration of about 290 mM, and citrate is present at a concentration of about 5 mM, and the pH is 4.

Also provided herein are methods of treating a respiratory disorder, inflammatory disorder, or obstructive airway disease, comprising delivering an aqueous pharmaceutical composition of indacaterol to the lungs of a patient in need thereof. The aqueous pharmaceutical composition may be any of the aqueous compositions provided herein. In some embodiments, the aqueous composition comprises about 20 weight percent to 99.9 weight percent water. In some embodiments, the respiratory disorder, inflammatory disorder, or obstructive airway disease is selected from the group consisting of COPD and asthma.

Also provided herein are methods of aerosolizing an aqueous liquid composition comprising indacaterol, or a pharmaceutically acceptable salt thereof. In some embodiments, the method comprises contacting a vibrating mesh with the aqueous liquid composition. In some embodiments, the method comprises aerosolizing the composition via a jet nebulizer. In some embodiments, the method comprises aerosolizing the composition via a soft mist inhaler. The aerosolizing method may be carried out with any of the aqueous compositions provided herein comprising indacaterol or a pharmaceutically acceptable salt thereof.

Also provided herein are methods of preparing a medicament comprising combining indacaterol or a pharmaceutically acceptable salt thereof and water in the presence of a solubilizing agent, wherein the medicament comprises about 20 weight percent to 99.9 weight percent water.

Also provided herein are methods of preparing an aqueous composition comprising indacaterol or a pharmaceutically acceptable salt thereof, comprising combining indacaterol or a pharmaceutically acceptable salt thereon and water in the presence of a solubilizing agent, wherein the water is present in the formulation in an amount of about 20 weight percent to 99.9 weight percent.

Also provided herein is a kit comprising indacaterol or a pharmaceutically acceptable salt thereof, a solubilizing agent and instructions for preparing an aqueous liquid composition thereof. In some embodiments the kit comprises indacaterol or a pharmaceutically acceptable salt thereof and the solubilizing agent in the same or separate containers. A kit provided herein may comprise a container, such as an ampule, vial, or cartridge, comprising an aqueous liquid composition comprising indacaterol or a pharmaceutically acceptable salt thereof, a solubilizing agent and water in an amount to provide an aqueous liquid composition. In some embodiments, the kit further comprises a device for aerosolizing an aqueous liquid composition. In some embodiments, the aqueous liquid composition comprises water in an amount of about 20 weight percent to 99.9 weight percent.

BRIEF DESCRIPTION OF THE DRAWINGS

FIG. 1 is a staggered chromatogram of indacaterol samples from the forced degradation experiment in Example 1 showing the minimal degradation of indacaterol samples in aqueous solutions over time.

FIG. 2A is a graph of the pH of formulas F2-F9 at various time points during a 90 day storage at low temperature showing that the pH is stable for the duration of the storage period.

FIG. 2B is a graph of the pH of formulas F2-F9 at various time points during a 90 day storage at room temperature showing that the pH is stable for the duration of the storage period.

FIG. 2C is a graph of the pH of formulas F2-F9 at various time points during a 90 day storage at high temperature showing that the pH is stable for the duration of the storage period.

FIG. 3A is a graph of indacaterol concentration in formulas F2-F9 at various time points during a 90 day storage period at low temperature showing that the concentration of indacaterol is maintained during the storage period.

FIG. 3B is a graph of indacaterol concentration in formulas F2-F9 at various time points during a 90 day storage period at room temperature showing that the concentration of indacaterol is maintained during the storage period.

FIG. 3C is a graph of indacaterol concentration in formulas F2-F9 at various time points during a 90 day storage period at high temperature showing that the concentration of indacaterol is maintained during the storage period.

FIG. 4 is a chromatogram showing product-related impurities associated with Formulation F5 and impurities in the indacaterol raw material.

FIG. 5 is a graph of delivered dose vs. charge volume for several aqueous indacaterol compositions.

FIG. 6 is a graph of deposited dose vs. charge volume for several aqueous indacaterol formulations.

DETAILED DESCRIPTION OF THE INVENTION

The disclosure encompasses aqueous compositions (which may also be referred to herein as aqueous formulations) of indacaterol, or a pharmaceutically acceptable salt thereof, that can, in some embodiments, include one or more excipients that are used, among other things, to modify indacaterol solubility, adjust tonicity, and control pH. The disclosure also relates to methods of treating respiratory disorders using the compositions, to methods of making the compositions, and to kits that contain the compositions.

The present disclosure relates to aqueous compositions of indacaterol, or a pharmaceutically acceptable salt thereof, to treat patients with respiratory diseases, including chronic obstructive pulmonary disorder (COPD) and asthma. The present invention further minimizes or eliminates the need for patient coordination and inspiratory effort by allowing indacaterol, by itself or in combination with other pharmaceutical agents and/or excipients, to be administered with devices such as breath-actuated vibrating mesh nebulizers. Due to the relatively low aqueous solubility reported for indacaterol, a suspension formulation may seem desirable. However, solution compositions offer particular advantages, such as an easier formulation and a higher concentration of indacaterol. A liquid indacaterol composition is provided with a sufficiently high indacaterol concentration to ensure a short dosing time and sufficient stability to be stored at room temperature. In some embodiments, the base form of indacaterol is used to allow solubility and stability evaluation without the effect of maleic acid that is present when the commonly known indacaterol maleate salt is used.

The design of such compositions is non-trivial due to solubility issues with indacaterol itself. While indacaterol is known to be soluble in organic solvents, including alcohols (e.g. methanol and ethanol), large amounts of these solvents are incompatible with safe and effective inhalable formulations. Ethanol formulations have a high osmotic pressure that can induce coughing in some cases, limiting their effectiveness in inhalable formulations. By contrast, the aqueous solutions disclosed herein can be tuned to be isotonic, which would allow them to be safely and effectively administered to patients, even those with significant breathing difficulties. Notably, many other commonly used LABA pharmaceuticals (e.g., formoterol) are not stable in aqueous solution at room temperature (see WO 2001/89480, incorporated herein by reference); by contrast, the aqueous compositions of indacaterol in the present disclosure are stable at room temperature for long periods of time. The stability of the indacaterol compositions also supports the use of additional pharmaceutical agents to be added to produce stable compositions with a combination of pharmaceuticals (e.g., indacaterol and glycopyrrolate).

In addition to the compositions provided herein, methods of treating diseases using the compositions, methods of making the compositions, and kits including the compositions are described.

It is understood that embodiments described herein as "comprising" may include "consisting" and/or "consisting essentially of" aspects and variations.

The disclosures of all publications, patents, and patent applications referred to herein are each hereby incorporated by reference in their entireties.

Definitions

Reference to "about" a value or parameter herein includes (and describes) variations that are directed to that value or parameter per se. For example, descriptions referring to "about X" includes descriptions of "X" per se and descriptions referring to from "about X" to "about Y" includes descriptions of from "X" to "Y" per se.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, the term "patient" is a mammal, including humans. A patient includes, but is not limited to, human, bovine, horse, feline, canine, rodent, or primate. In some embodiments, the patient is human. The patient (such as a human) may have advanced disease or lesser extent of disease.

As used herein, the term "effective amount" intends such amount of a composition which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered composition may optionally be lowered due to the combined action (e.g., additive or synergistic effects) of the composition.

As used herein, "pharmaceutically acceptable," refer to a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, "weight percent" refers to the percentage of a component of a composition by weight. A component that is present at "5 weight percent" takes up 5%, by weight, of the total weight of the composition. As used herein, "% w/v" refers to a concentration defined by "g solute/100 mL of solution." For example, a composition that comprises 0.5% w/v of cyclodextrin contains 0.5 g of cyclodextrin per 100 mL of solution. As used herein, "% v/v" refers to a concentration of a liquid in another liquid by comparing their relative volumes. For example, a composition that comprises 20% v/v of ethanol contains 20 mL of ethanol per 100 mL of the total solution.

The term "indacaterol" refers to (R)-5-[2-(5,6-Diethylindan-2-ylamino)-1-hydroxyethyl]-8hydroxy-1H-quinolin-2-one, which may exist as the free base form or a salt thereof. One example of a salt of indacaterol is indacaterol maleate. The structure of indacaterol is shown below:

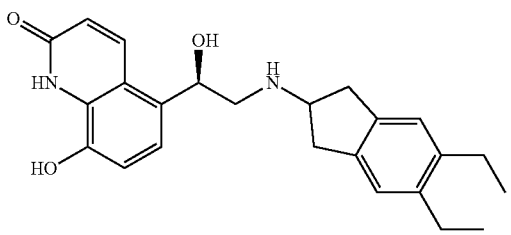 [SMILES: CCc1cc2c(cc1CC)CC(NC[C@H](O)c1ccc(O)c3[nH]c(=O)ccc13)C2]

COMPOSITIONS

The compositions provided are notable in that indacaterol is substantially dissolved and stable over a significant period of time in an aqueous solution. In some embodiments, the stability and/or extent of degradation is assessed by appearance of the composition. In some embodiments, the stability and/or extent of degradation is assessed by pH of the composition. In some embodiments, the stability and/or extent of degradation is assessed by concentration of indacaterol in the composition. In some embodiments, the stability and/or extent of degradation is assessed by the concentration or amount of impurities in the composition. In some embodiments, the stability and/or extent of degradation is assessed by osmolality of the composition. These examples are not intended to be limiting, as a person of skill in the art may be aware of other methods to assess the stability and/or extent of degradation. In some embodiments, provided herein are aqueous compositions comprising indacaterol, or a pharmaceutically acceptable salt there, wherein the compositions exhibit less than 10%, 20%, 30%, 40%, or 50% indacaterol degradation upon storage for a period of a year. In some embodiments, the compositions exhibit less than 10%, 20%, 30%, 40%, or 50% indacaterol degradation upon storage for a period of 2 years. In some embodiments, the compositions exhibit less than 10%, 20%, 30%, 40%, or 50% indacaterol degradation upon storage for a period of 5 years. In some embodiments, the compositions exhibit less than 10%, 20%, 30%, 40%, or 50% indacaterol degradation upon storage for a period of 10 years. In some embodiments, the indacaterol is in the base form. In some embodiments, the indacaterol is present as a pharmaceutically acceptable salt. In some embodiments, the indacaterol is present as indacaterol maleate. In some embodiments, the storage conditions are 40° C. with 75% relative humidity. In some embodiments, the storage conditions are 25° C. with 60% relative humidity. In some embodiments, the storage conditions is 5° C. In some embodiments, the compositions exhibit less than 10%, 20%, 30%, 40%, or 50% indacaterol degradation upon storage for a period of 30, 60, or 90 days. In some embodiments, the compositions exhibit less than 10%, 20%, 30%, 40%, or 50% indacaterol degradation upon storage for a period of 1, 2, 3, 4, or 5 weeks.

In some embodiments, the aqueous compositions comprising indacaterol, or a pharmaceutically acceptable salt thereof, comprise at least 5% and up to about any one of 20%, 30%, 40%, 50%, 60%, 70%, 80%, 90%, 95%, 99%, or 99.9% water by weight. In some embodiments, the aqueous compositions comprising indacaterol, or a pharmaceutically acceptable salt thereof, comprise more than about any one of 20%, 30%, 40%, 50%, 60%, 70%, 80%, 90%, 95%, 99% water by weight. In some embodiments, the aqueous compositions comprising indacaterol, or a pharmaceutically acceptable salt thereof, comprise about 20%, 30%, 40%, 50%, 60%, 70%, 80%, 90%, 95%, or 99% water by weight. In some embodiments, the compositions comprise from about any one of 20%, 30%, 40%, 50%, 60%, 70%, 80% or 90% to about 99.9% water by weight. In some embodiments, the compositions comprise from about any one of 20%, 30%, 40%, 50%, 60%, 70%, 80% or 90% to about 95% water by weight. In some embodiments, the compositions comprise from about any one of 20%, 30%, 40%, 50%, 60%, 70% or 80% to about 90% water by weight. In some embodiments, the compositions comprise from about any one of 20%, 30%, 40%, 50%, 60% or 70% to about 80% water by weight. In some embodiments, the compositions comprise from about any one of 20%, 30%, 40%, 50% or 60% to about 70% water by weight. In some embodiments, the compositions comprise from about any one of 20%, 30%, 40%, or 50% to about 60% water by weight. In some embodiments, the compositions comprise from about any one of 20%, 30%, or 40% to about 50% water by weight.

In some embodiments, provided is an aqueous composition comprising indacaterol, or a pharmaceutically acceptable salt thereof, at a concentration from about 10 µg/mL to about 2 mg/mL. In some embodiments, the indacaterol is present at a concentration up to about 2 mg/mL, up to about 1 mg/mL, up to about 800 µg/mL, up to about 600 µg/mL, up to about 400 µg/mL, up to about 200 µg/mL, up to about 50 µg/mL, or up to about 10 µg/mL. In some embodiments, the indacaterol is at a concentration from about 10 µg/mL to about 2 mg/mL, from about 10 µg/mL to about 1.5 mg/mL, from about 10 µg/mL to about 1 mg/mL, from about 10 µg/mL to 800 µg/mL, from about 10 µg/mL to about 600 µg/mL, from about 10 µg/mL to about 400 µg/mL, from about 10 µg/mL to about 200 µg/mL, from about 50 µg/mL to about 1 mg/mL, from about 50 µg/mL to about 800 µg/mL, from about 50 µg/mL to about 600 µg/mL, from about 50 µg/mL to about 400 µg/mL, from about 50 µg/mL to about 200 µg/mL, from about 200 µg/mL to about 1 mg/mL, from about 200 µg/mL to about 800 µg/mL, from about 200 µg/mL to about 600 µg/mL, from about 200 µg/mL to about 400 µg/mL, from about 400 µg/mL to about 1 mg/mL, from about 400 µg/mL to about 800 µg/mL, from about 400 µg/mL to about 600 µg/mL, from about 600 µg/mL to about 1 mg/mL, or from about 600 µg/mL to about 800 µg/mL.

It is to be understood that in the context of this disclosure all concentrations for indacaterol are given for the indacaterol free base, regardless of the form of indacaterol that is added to the composition. For example, a composition that is made using 500 µg/mL of indacaterol maleate contains 384.6 µg/mL of indacaterol free base (the molecular weight of indacaterol maleate is 508.6 g/mol, and the molecular weight of indacaterol free base is 392.5 g/mol, 508.6 g/mol/392.5 g/mol=1.3, and 500 µg/mL/1.3=384.6 µg/mL). Similarly, it is to be understood that in the context of this disclosure all dosages referred to herein are given for the indacaterol free base, regardless of the form of indacaterol that is administered.

In some embodiments, the indacaterol is present in the form of an indacaterol salt. In some embodiments, the indacaterol salt is a water soluble salt of indacaterol. In some embodiments, the indacaterol salt has a solubility in water of at least 100 µg/mL, at least 200 µg/mL, at least 300 µg/mL, or at least 400 µg/mL in water. In some embodiments, the indacaterol salt has a solubility of at least 200 or at least 300 µg/mL in water. In some embodiments the indacaterol salt has a solubility of at least 100 µg/mL, at least 200 µg/mL, at least 300 µg/mL, or at least 400 µg/mL in water at a pH of 3. In some embodiments, the indacaterol salt has a solubility of at least 100 µg/mL, at least 200 µg/mL, or at least 300

µg/mL at a pH of 4. In some embodiments, the indacaterol salt has a solubility of at least 100 µg/mL at a pH of 5. In some embodiments, the indacaterol salt is selected from the group consisting of indacaterol acetate, indacaterol tartrate, and indacaterol citrate. In some embodiments, the indacaterol salt is indacaterol citrate. Also provided herein are pharmaceutical compositions comprising an indacaterol salt such as indacaterol citrate. In some embodiments, the pharmaceutical composition is an aqueous pharmaceutical composition suitable for inhalation. Any of the methods detailed herein may comprise an indacaterol salt, such as indacaterol citrate, or a pharmaceutical composition comprising the same.

In some embodiments, the aqueous composition comprises a solubilizing agent. In some embodiments, the solubilizing agent is a cyclodextrin. In some embodiments, the cyclodextrin is sulfobutylether-β-cyclodextrin (SBE-β-CD). In some embodiments, the cyclodextrin is present in an amount from about 0.1% w/v to about 10% w/v. In some embodiments, the cyclodextrin is present from about 0.1% w/v to about 5% w/v. In some embodiments, the cyclodextrin is present from about 0.1% w/v to about 1% w/v. In some embodiments, the cyclodextrin is present from about 0.25% w/v to about 1% w/v. In some embodiments, the cyclodextrin is present from about 0.25% w/v to about 5% w/v. In some embodiments, the cyclodextrin is present from about 0.25% w/v to about 10% w/v.

In some embodiments, the aqueous composition comprises one or more tonicity modifiers. In some embodiments, the one or more tonicity modifiers are sodium chloride and mannitol. In some embodiments, the one or more tonicity modifier is either sodium chloride or mannitol. In some embodiments, the one or more tonicity modifier is mannitol. In some embodiments, the aqueous composition is isotonic. In some embodiments, the one or more tonicity modifier is present at a concentration from about any one of 100 mM, 200 mM, 300 mM or 400 mM to about 500 mM. In some embodiments, the one or more tonicity modifier is present at a concentration from about any one of 100 mM, 200 mM or 300 mM to about 400 mM. In some embodiments, the one or more tonicity modifier is present at a concentration from about 100 mM or 200 mM to about 300 mM. In some embodiments, the one or more tonicity modifier is present at a concentration from about 100 mM to about 200 mM. In some embodiments, two or more tonicity modifiers may each be individually present at any of ranges disclosed for a single tonicity modifier.

In some embodiments, the aqueous composition comprises a buffer. In some embodiments, the buffer is a citrate-containing buffer. In some embodiments, the buffer is prepared from citric acid and trisodium citrate. In some embodiments, the buffer is prepared from citric acid and a strong base. In some embodiments, the composition is buffered to a pH from 2 to 6. In some embodiments, the composition is buffered to a pH from 3 to 6. In some embodiments, the composition is buffered to a pH from 4 to 6. In some embodiments, the composition is buffered to a pH from 5 to 6. In some embodiments, the composition is buffered to a pH from 2 to 5. In some embodiments, the composition is buffered to a pH from 3 to 5. In some embodiments, the composition is buffered to a pH from 4 to 5. In some embodiments, the composition is buffered to a pH from 2 to 4. In some embodiments, the composition is buffered to a pH from 3 to 4. In some embodiments, the composition is buffered to a pH from 2 to 3. In some embodiments, the composition is buffered to a pH from 3.5 to 4.5. In some embodiments, the composition is buffered to a pH of about 4. In some embodiments, the composition is buffered to a pH of less than 8. In some embodiments, the composition is buffered to a pH from 2 to 8.

In some embodiments, the aqueous composition comprises a co-solvent. In some embodiments, the co-solvent is ethanol or ethylene glycol. In some embodiments, the co-solvent is present in an amount from about 0.1% v/v to about 10% v/v, from about 0.1% v/v to about 5% v/v, from about 0.1% v/v to about 2.5% v/v, from about 0.1% v/v to about 1% v/v, from about 0.5% v/v to about 5% v/v, from about 0.5% v/v to about 2.5% v/v, from about 0.5% v/v to about 1% v/v, from about 1% v/v to about 5% v/v, or from about 1% v/v to about 2.5% v/v.

In some embodiments, the aqueous composition comprises a preservative. In some embodiments, the preservative comprises benzalkonium chloride. In some embodiments, the preservative comprises ethylenediaminetetraacetic acid (EDTA). In some embodiments, the composition comprises two or more preservatives. In some embodiments, the composition comprises benzalkonium chloride and EDTA. In some embodiments, the preservative is present at a concentration from about 0.001% to about 0.1%. In some embodiments, the preservative is present at a concentration of about 0.01% to about 0.1%. In some embodiments, the preservative is present at a concentration of about 0.001% to about 0.01%. In cases with multiple preservatives, each preservative may be individually present at any of the ranges recited above.

In some embodiments, the aqueous composition comprises water and indacaterol as a free base. In some embodiments, the aqueous composition comprises water and a pharmaceutically acceptable salt of indacaterol, such as indacaterol maleate. In some embodiments, the aqueous composition comprises water, indacaterol, or a pharmaceutically acceptable salt thereof, and a solubilizing agent. In some embodiments, the aqueous composition comprises water, indacaterol, or a pharmaceutically acceptable salt thereof, and a buffer. In some embodiments, the aqueous composition comprises water, indacaterol, or a pharmaceutically acceptable salt thereof, and a tonicity modifier. In some embodiments, the aqueous composition comprises water, indacaterol, or a pharmaceutically acceptable salt thereof, and a co-solvent. In some embodiments, the aqueous composition comprises water, indacaterol, or a pharmaceutically acceptable salt thereof, a solubilizing agent, and a buffer. In some embodiments, the aqueous composition comprises water, indacaterol, or a pharmaceutically acceptable salt thereof, a solubilizing agent, and a tonicity modifier. In some embodiments, the aqueous composition comprises water, indacaterol, or a pharmaceutically acceptable salt thereof, a solubilizing agent, and a co-solvent. In some embodiments, the aqueous composition comprises water, indacaterol, or a pharmaceutically acceptable salt thereof, a buffer, and a tonicity modifier. In some embodiments, the aqueous composition comprises water, indacaterol, or a pharmaceutically acceptable salt thereof, a buffer, and a co-solvent. In some embodiments, the aqueous composition comprises water, indacaterol, or a pharmaceutically acceptable salt thereof, a solubilizing agent, a buffer, and a tonicity modifier. In some embodiments, the aqueous composition comprises water, indacaterol, or a pharmaceutically acceptable salt thereof, a solubilizing agent, a buffer, and a co-solvent. In some embodiments, the aqueous composition comprises water, indacaterol, or a pharmaceutically acceptable salt thereof, a solubilizing agent, a tonicity modifier, and a co-solvent. In some embodiments, the aqueous composition comprises water, indacaterol, or a pharmaceutically acceptable salt thereof, a buffer, a tonicity modifier, and a co-solvent. Each of the water, indacaterol, or a pharmaceutically acceptable salt thereof, solubilizing agent, buffer, tonicity modifier, and co-solvent may be present in an aqueous composition any amounts as disclosed herein. In some embodiments, the aqueous composition comprises water, indacaterol, or a pharmaceutically acceptable salt thereof, and a preservative. In some embodiments, the aqueous composition comprises water, indacaterol, or a pharmaceutically acceptable salt thereof, a solubilizing agent, and a preservative. In some embodiments, the aqueous composition comprises water, indacaterol, or a pharmaceutically acceptable salt thereof, a buffer, and a preservative. In some embodiments, the aqueous composition comprises water, indacaterol, or a pharmaceutically acceptable salt thereof, a tonicity modifier, and a preservative. In some embodiments, the aqueous composition comprises water, indacaterol, or a pharmaceutically acceptable salt thereof, a co-solvent, and a preservative. In some embodiments, the aqueous composition comprises water, indacaterol, or a pharmaceutically acceptable salt thereof, a solubilizing agent, a buffer, and a preservative. In some embodiments, the aqueous composition comprises water, indacaterol, or a pharmaceutically acceptable salt thereof, a solubilizing agent, a tonicity modifier, and a preservative. In some embodiments, the aqueous composition comprises water, indacaterol, or a pharmaceutically acceptable salt thereof, a solubilizing agent, a co-solvent, and a preservative. In some embodiments, the aqueous composition comprises water, indacaterol, or a pharmaceutically acceptable salt thereof, a buffer, a tonicity modifier, and a preservative. In some embodiments, the aqueous composition comprises water, indacaterol, or a pharmaceutically acceptable salt thereof, a buffer, a co-solvent, and a preservative. In some embodiments, the aqueous composition comprises water, indacaterol, or a pharmaceutically acceptable salt thereof, a tonicity modifier, a co-solvent, and a preservative. In some embodiments, the aqueous composition comprises water, indacaterol, or a pharmaceutically acceptable salt thereof, a solubilizing agent, a buffer, a tonicity modifier, and a preservative. In some embodiments, the aqueous composition comprises water, indacaterol, or a pharmaceutically acceptable salt thereof, a solubilizing agent, a buffer, a co-solvent, and a preservative. In some embodiments, the aqueous composition comprises water, indacaterol, or a pharmaceutically acceptable salt thereof, a solubilizing agent, a tonicity modifier, a co-solvent, and a preservative. In some embodiments, the aqueous composition comprises one or more of water, indacaterol or a pharmaceutically acceptable salt thereof, a buffer, a tonicity modifier, a co-solvent, and a preservative. In some embodiments, the aqueous composition comprises water, indacaterol or a pharmaceutically acceptable salt thereof, and one or more of the components listed above. Each possible combination of three or more components is to be considered as though each were specifically and individually listed. Each of the water, indacaterol or a pharmaceutically acceptable salt thereof, solubilizing agent, buffer, tonicity modifier, co-solvent, and preservative may be present in any amounts as disclosed herein.

In some embodiments, the composition comprises indacaterol and an additional pharmaceutical agent. In some embodiments, the additional pharmaceutical agent is a long acting muscarinic antagonist and/or an inhaled corticosteroid. In some embodiments, the long acting muscarinic antagonist is tiotropium or a pharmaceutically acceptable salt thereof. In some embodiments, the long acting muscarinic antagonist is tiotropium bromide. In some embodiments, the long acting muscarinic antagonist is glycopyrrolate or a pharmaceutically acceptable salt thereof. In some embodiments, the long acting muscarinic antagonist is glycopyrronium bromide. In some embodiments, the inhaled corticosteroid is mometasone or a pharmaceutically acceptable salt thereof. In some embodiments, an aqueous combination provided herein comprising indacaterol or a pharmaceutically acceptable salt thereof further comprises two additional pharmaceutical agents. In some embodiments, the additional pharmaceutical agents comprise a long acting muscarinic agent and an inhaled corticosteroid. In some embodiments, an aqueous composition provided herein comprises indacaterol, glycopyrronium, and mometasone or pharmaceutically acceptable salts of any of the foregoing.

In some embodiments, the additional pharmaceutical agent is present at a concentration from about 10 µg/mL to about 2 mg/mL. In some embodiments, the additional pharmaceutical agent is present at a concentration up to about 2 mg/mL, up to about 1 mg/mL, up to about 800 µg/mL, up to about 600 µg/mL, up to about 400 µg/mL, up to about 200 µg/mL, up to about 50 µg/mL, or up to about 10 µg/mL. In some embodiments, the additional pharmaceutical agent is present at a concentration from about 10 µg/mL to about 2 mg/mL, from about 10 µg/mL to about 1.5 mg/mL, from about 10 µg/mL to about 1 mg/mL, from about 10 µg/mL to 800 µg/mL, from about 10 µg/mL to about 600 µg/mL, from about 10 µg/mL to about 400 µg/mL, from about 10 µg/mL to about 200 µg/mL, from about 50 µg/mL to about 1 mg/mL, from about 50 µg/mL to about 800 µg/mL, from about 50 µg/mL to about 600 µg/mL, from about 50 µg/mL to about 400 µg/mL, from about 50 µg/mL to about 200 µg/mL, from about 200 µg/mL to about 1 mg/mL, from about 200 µg/mL to about 800 µg/mL, from about 200 µg/mL to about 600 µg/mL, from about 200 µg/mL to about 400 µg/mL, from about 400 µg/mL to about 1 mg/mL, from about 400 µg/mL to about 800 µg/mL, from about 400 µg/mL to about 600 µg/mL, from about 600 µg/mL to about 1 mg/mL, or from about 600 µg/mL to about 800 µg/mL.

In certain embodiments, the composition is a pharmaceutical formulation which is present in a unit dosage form. In one variation, the unit dosage form comprises one or more additional pharmaceutical agents.

METHODS OF MAKING

Provided herein are methods of making the compositions described herein. In some embodiments, the method of making a composition as described herein comprises steps a) to f):

a) adding indacaterol, or a pharmaceutically acceptable salt thereof, to a liquid comprising water and a solubilizing agent to form a mixture; and
b) adjusting a pH of the mixture to obtain the composition.

In some embodiments, the mixture further comprises one or more excipients are selected from the group consisting of a buffer, a co-solvent, a tonicity modifier, and a preservative. In some embodiments, step b) comprises waiting for the mixture to reach equilibrium. In some embodiments, step b) lasts a period of time from 12 to 72 hours. In some embodiments, the pH is adjusted using a strong acid and a strong base. In some embodiments, the strong acid is HCl. In some embodiments, the strong base is NaOH. In some embodiments, step b) further comprises adding an acid or acid form of a buffer. In some embodiments, the acid or acid form of a buffer is added until the mixture has a pH equal to or below 4.0, 3.0, or 2.0. In some embodiments, the acid or acid form of a buffer is added until the mixture has a pH equal to or below 2.0. In some embodiments, the acid or acid form of a buffer is added until the mixture has a pH equal to or below 2.0 before waiting for the mixture to reach equilibrium. In some embodiments, the acid or acid form of a buffer is citric acid. In some embodiments, the mixture further comprises one or more additional pharmaceutical agents. In some embodiments, the one or more additional pharmaceutical agents comprise a long acting muscarinic antagonist. In some embodiments, the one or more additional pharmaceutical agents comprise tiotropium or a salt thereof. In some embodiments, the one or more additional pharmaceutical agents comprise glycopyrrolate or a salt thereof.

METHODS OF USE

In some embodiments, the aqueous composition is used to treat a patient. In some embodiments, the composition is delivered to a patient in need thereof as an aerosol. In some embodiments, the aerosol is generated by contacting the aqueous composition with a vibrating mesh. In some embodiments, the API of the aqueous composition is delivered to the lungs of a patient in need thereof. In some embodiments, the composition acts as a bronchodilator.

In some embodiments, a method is provided for the delivery of indacaterol to the lungs of a patient in need thereof, wherein the delivery is accomplished via low tidal breathing. In some embodiments, the patient has difficulty generating sufficient inspiratory effort to properly use dry powder inhalers or has significant cough caused by the irritation of dry powders. In some embodiments, the patient has difficulty generating a pressure drop of 1 kPa or more (Clark, A. R., et al., *J Aerosol Med Pulm Drug Deliv*, (2020) 33, 1-11). In some embodiments, the patient has difficulty with the coordination of device actuation and inhalation that is required for proper usage of dry powder inhalers, metered dose pressurized inhalers, and/or soft mist inhalers. In some embodiments, the patient is an elderly or pediatric patient. In some embodiments, the elderly patient is 65 years old or older. In some embodiments, the elderly patient is 75 years old or older. In some embodiments, the elderly patient is between 75 and 100 years old. In some embodiments, the patient is an adult. In some embodiments, the patient is younger than 65 years old. In some embodiments, the patient is younger than 50 years old. In some embodiments, the patient is younger than 40 years old. In some embodiments, the patient is a young adult. In some embodiments, the patient is younger than 30 years old. In some embodiments, the patient is younger than 25 years old. In some embodiments, the patient is younger than 20 years old. In some embodiments, the patient is a teenager. In some embodiments, the patient is younger than 15 years old. In some embodiments, the patient is older than 2 years old. In some embodiments, the patient has COPD and/or asthma and/or emphysema.

In some embodiments, the aqueous compositions are used in the treatment of a patient with a respiratory disorder. In some embodiments, the aqueous compositions are used in the treatment of patient with an inflammatory disorder, such as an inflammatory disorder of the airways and/or lungs. In some embodiments, the aqueous compositions are used in the treatment of patient with an obstructive airway disease. In some embodiments, the patient has one or more of a respiratory disorder, an inflammatory disorder, and/or an obstructive airway disease. In some embodiments, the aqueous compositions are used to treat COPD. In some embodiments, the aqueous compositions are used to treat asthma. In some embodiments, the aqueous compositions are used to treat COPD and asthma. In some embodiments, the aqueous compositions are used to treat emphysema. In some embodiments, the compositions are used to treat COPD and emphysema. In some embodiments, the treatment includes the prevention or delayed occurrence of symptoms related to the respiratory disorder, inflammatory disorder, or obstructive airway disease, such as in a patient at risk of developing such symptoms.

The composition is administered to the patient in an effective amount to treat the desired respiratory disorder, inflammatory disorder, or obstructive airway disease. In some embodiments, the composition is administered to the patient daily. In some embodiments, the composition is administered to the patient twice daily. In some embodiments, the dose of indacaterol is from 20 to 300 µg. In some embodiments, the dose of indacaterol is from 50 to 200 µg. In some embodiments, the dose of indacaterol is from 65 to 90 µg. In some embodiments, the dose of indacaterol is from 70 to 80 µg. In some embodiments, the dose of indacaterol is 75 µg. In some embodiments, the composition is intended as a maintenance treatment of a respiratory disorder, inflammatory disorder such as asthma, or obstructive airway disease such as COPD.

In some embodiments, the patient receiving the composition is the subject of one or more additional therapies and/or treatments for a respiratory disorder. In some embodiments, the respiratory disorder is asthma. In some embodiments, the respiratory disorder is COPD. In some embodiments, the respiratory disorder is emphysema. In some embodiments, the respiratory disorder is seasonal allergies.

The composition can be administered to a patient in need thereof with a variety of devices. In some embodiments, the device is an inhaler device or a nebulizer. In some embodiments, the device is a soft mist inhaler, a jet nebulizer, or a vibrating mesh device. In some embodiments, the device is a jet nebulizer. In some embodiments, the device is a soft mist inhaler. In some embodiments, the device is a mesh nebulizer.

In some embodiments, the aqueous composition is included as part of a kit that includes a device used to aerosolize the formulation. In some embodiments, the device comprises a vibrating mesh. In some embodiments, the kit comprises indacaterol or a pharmaceutically acceptable salt thereof, a solubilizing agent and instructions for preparing an aqueous liquid composition thereof. In some embodiments, the kit comprises indacaterol or a pharmaceutically acceptable salt thereof and the solubilizing agent in the same or separate containers. A kit provided herein may comprise a container, such as an ampule, vial, or cartridge, comprising an aqueous liquid composition comprising indacaterol or a pharmaceutically acceptable salt thereof, a solubilizing agent and water in an amount to provide an aqueous liquid composition. In some embodiments, the kit further comprises a device for aerosolizing an aqueous liquid composition. In some embodiments, the aqueous liquid composition comprises water in an amount of about 20 weight percent to 99.9 weight percent.

The kits may be in unit dosage forms, bulk packages (e.g., multi-dose packages) or sub-unit doses. For example, kits may be provided that contain sufficient dosages of a composition as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the composition and instructions for use.

ENUMERATED EMBODIMENTS

Embodiment 1. A pharmaceutical composition comprising from about 20 weight percent to 99.9 weight percent water; and indacaterol, or a pharmaceutically acceptable salt thereof, present at a concentration of 10 μg/mL to 2 mg/mL.

Embodiment 2. The composition of embodiment 1, wherein the indacaterol is present as a free base.

Embodiment 3. The composition of embodiment 1 or 2, further comprising a solubilizing agent.

Embodiment 4. The composition of embodiment 3, wherein the solubilizing agent is a complexing agent.

Embodiment 5. The composition of embodiment 4, wherein the complexing agent is a cyclodextrin.

Embodiment 6. The composition of embodiment 5, wherein the cyclodextrin is selected from the group consisting of β-CD, SBE-β-CD, HP-β-CD, and γ-CD.

Embodiment 7. The composition of embodiment 5 or 6, wherein the cyclodextrin is present in an amount from about 0.1% w/v to about 10% w/v.

Embodiment 8. The composition of embodiment 7, wherein cyclodextrin is present in an amount of about 0.25% w/v to about 1% w/v.

Embodiment 9. The composition of any one of embodiments 1-8, further comprising one or more tonicity modifiers.

Embodiment 10. The composition of embodiment 9, wherein the one or more tonicity modifiers is mannitol.

Embodiment 11. The composition of embodiment 9, wherein the one or more tonicity modifiers is sodium chloride.

Embodiment 12. The composition of any one of embodiments 9-11, wherein the composition comprises two or more tonicity modifiers, each individually present at a concentration of about 50 mM to about 500 mM.

Embodiment 13. The composition of embodiment 12, wherein a first tonicity modifier is present at a concentration of about 200 mM to about 350 mM.

Embodiment 14. The composition of embodiment 12 or 13, wherein a second tonicity modifier is present at a concentration of 100 mM to 200 mM.

Embodiment 15. The composition of any one of embodiments 1-14, further comprising a co-solvent.

Embodiment 16. The composition of embodiment 15, wherein the co-solvent is an alcohol.

Embodiment 17. The composition of embodiment 16, wherein the co-solvent is selected from the group consisting of ethanol and ethylene glycol.

Embodiment 18. The composition of any one of embodiments 15-17, wherein the co-solvent is present in an amount from about 0.1% v/v to about 10% v/v.

Embodiment 19. The composition of any one of embodiments 1-18, further comprising a buffer.

Embodiment 20. The composition of embodiment 19, wherein the buffer comprises an anion selected from the group consisting of acetate, bromide, chloride, citrate, furoate, fumarate, maleate, malate, propionate, succinate, sulfate, tartrate, and xinafoate.

Embodiment 21. The composition of embodiment 19 or 20, wherein the buffer is prepared from a combination of citric acid and trisodium citrate or a combination of citric acid and sodium hydroxide.

Embodiment 22. The composition of any one of embodiments 1-21, wherein the composition has a pH from 2 to 6.

Embodiment 23. The composition of any one of embodiments 1-22, wherein the composition has a pH from 3 to 5.

Embodiment 24. The composition of any one of embodiments 1-23, wherein the composition has a pH from 3.5 to 4.5.

Embodiment 25. The composition of any one of embodiments 1-24, further comprising one or more additional pharmaceutical agents.

Embodiment 26. The composition of embodiment 25, wherein the additional pharmaceutical agent is a long acting muscarinic antagonist or an inhaled corticosteroid.

Embodiment 27. The composition of embodiment 26, wherein the long acting muscarinic antagonist is tiotropium, glycopyrrolate, or a pharmaceutically acceptable salt of either of the foregoing.

Embodiment 28. The composition of embodiment 27, wherein the long acting muscarinic antagonist is tiotropium bromide or glycopyrronium bromide.

Embodiment 29. The composition of embodiment 26, wherein the inhaled corticosteroid is mometasone or a pharmaceutically acceptable salt thereof.

Embodiment 30. The composition of embodiment 25, wherein there are two additional pharmaceutical agents.

Embodiment 31. The composition of embodiment 30, wherein the additional pharmaceutical agents are a long acting muscarinic antagonist and an inhaled corticosteroid.

Embodiment 32. The composition of embodiment 31, wherein the long acting muscarinic antagonist is glycopyrrolate or a pharmaceutically acceptable salt thereof and the inhaled corticosteroid is mometasone or a pharmaceutically acceptable salt thereof.

Embodiment 33. The composition of any one of embodiments 1-32, wherein the indacaterol exhibits less than 5% degradation for a period of 90 days.

Embodiment 34. The composition of embodiment 33, wherein the composition is stored at a temperature of about 25° C.

Embodiment 35. The composition of embodiment 33 or 34 wherein the composition is stored at a relative humidity of about 60%.

Embodiment 36. The composition of embodiment 1 or 2, further comprising
a complexing agent;
one or more tonicity modifiers; and
a buffer.

Embodiment 37. The composition of embodiment 36, wherein
the complexing agent is a cyclodextrin;
one tonicity modifier is mannitol; and
the buffer comprises citrate.

Embodiment 38. The composition of embodiment 37, wherein
the cyclodextrin is present in an amount from 0.25% w/v to 1% w/v;
mannitol is present at a concentration from 100 mM to 500 mM; and
the pH is from 3 to 6.

Embodiment 39. The composition of embodiment 38, wherein
cyclodextrin is present in an amount of 0.5% w/v;
mannitol is present at a concentration of 290 mM; and
citrate is present at a concentration of 5 mM, and
wherein the pH is about 4.0.

Embodiment 40. A method of treating a respiratory disorder, inflammatory disorder, or obstructive airway disease, comprising
delivering an aqueous pharmaceutical composition of indacaterol or a pharmaceutically acceptable salt thereof to the lungs of a patient in need thereof.

Embodiment 41. The method of embodiment 40, wherein the aqueous pharmaceutical composition comprises 20 weight percent to 99.9 weight percent water.

Embodiment 42. The method of embodiment 40 or 41, wherein the respiratory disorder, inflammatory disorder, or obstructive airway disease is selected from the group consisting of COPD and asthma.

Embodiment 43. The method of any one of embodiments 40-42, wherein a breath-actuated vibrating mesh nebulizer is used to aerosolize the pharmaceutical composition.

Embodiment 44. A method of aerosolizing an aqueous liquid composition of indacaterol or a pharmaceutically acceptable salt thereof, comprising contacting a vibrating mesh with the liquid formulation.

Embodiment 45. A method of aerosolizing an aqueous liquid composition of indacaterol or a pharmaceutically acceptable salt thereof, comprising aerosolizing the composition via a jet nebulizer or a soft mist inhaler.

Embodiment 46. A method of preparing a medicament comprising mixing indacaterol or a pharmaceutically acceptable salt thereof and water in the presence of a solubilizing agent, wherein the medicament comprises 20 weight percent to 99.9 weight percent water.

Embodiment 47. A method of preparing an aqueous composition of indacaterol or a pharmaceutically acceptable salt thereof, comprising mixing indacaterol and water in the presence of a solubilizing agent, wherein the water is present in the formulation in an amount of 20 weight percent to 99.9 weight percent.

Embodiment 48. A method of preparing an aqueous composition of indacaterol, or a pharmaceutically acceptable salt thereof, comprising steps a) and b):
a) adding indacaterol, or a pharmaceutically acceptable salt thereof, to a liquid comprising water and a solubilizing agent to form a mixture; and
b) adjusting a pH of the mixture to obtain the composition.

Embodiment 49. The method of embodiment 48, wherein step b) comprises adding an acid or acid form of a buffer, wherein the acid or acid form of the buffer is added until the water has a pH equal to or below 3.0.

Embodiment 50. The method of embodiment 49, wherein the acid or acid form of a buffer is added until the water has a pH equal to or below 2.0.

Embodiment 51. The method of any one of embodiments 48-50, wherein the mixture further comprises one or more additional pharmaceutical agents.

Embodiment 52. The method of embodiment 51, wherein the mixture comprises one additional pharmaceutical agent.

Embodiment 53. The method of embodiment 52, wherein the additional pharmaceutical agent is a long acting muscarinic antagonist.

Embodiment 54. The method of embodiment 52 or 53, wherein the additional pharmaceutical agent is tiotropium, glycopyrrolate, or a salt of either of the foregoing.

Embodiment 55. A kit comprising
an aqueous, pharmaceutical composition of indacaterol or a pharmaceutically acceptable salt thereof; and
a device for aerosolizing the pharmaceutical composition.

Embodiment 56. The kit of embodiment 55, wherein the water is present in an amount of 20 weight percent to 99.9 weight percent.

EXAMPLES

Materials used below were purchased commercially unless indicated otherwise. Indacaterol (base) was purchased from Cayman Chemicals. Indacaterol maleate was purchased from AChemBlock.

Example 1—Forced Degradation Study

A degraded sample panel was prepared to identify indacaterol degradation pathways and products. Stress conditions are outlined in Table 1.

TABLE 1

Sample properties in forced degradation study

| Sample No. | Sample Description | Stress condition | Indacaterol base concentration (µg/mL) | Diluent/solvent |
|---|---|---|---|---|
| 1 | Control | — | 10 | MeOH:H$_2$O (50:50, v:v) |
| 2 | Acidic hydrolysis | HCl, 1M | 10 | |
| 3 | Basic hydrolysis | NaOH, 1M | 10 | |
| 4 | Oxidation | H$_2$O$_2$, 1.2% | 10 | |

One of 6N HCl, 6N NaOH, or 30% H$_2$O$_2$ (aqueous) were added to a suitable volume of 100 µg/mL indacaterol and diluted with water:methanol (50:50, v:v) to achieve a final indacaterol concentration of 10 µg/mL. Samples were stored at ambient temperature. At specified time points, acidic and basic hydrolysis (1 N HCl and 1 N NaOH, respectively) samples were neutralized (H$_2$O$_2$ samples were not quenched) and reversed-phase high performance liquid chromatography (RP-HPLC) was used to quantitate indacaterol impurities. All samples were diluted to 5 µg/mL prior to RP-HPLC analysis. Method parameters are outlined in Table 2.

TABLE 2

RP-HPLC Impurity Method Parameters (Examples 1-7)

| Column | Purospher Star RP-18 (Hibar RT), 5 µm, 4 × 125 mm |
|---|---|
| Reference Standard | Indacaterol Base |
| Mobile Phase A | 0.1% TFA in Water |
| Mobile Phase B | 0.1% TFA in ACN |
| Diluent | 50:50 Water:Methanol |
| Autosampler Temp. | 20° C. |
| Column Temp. | 40° C. |
| Injection Volume | 60 µL |
| Wavelength | 254 nm and 270 nm |
| Flow Rate | 0.8 mL/min |
| Run Time | 36 minutes |
| Elution Mode | Gradient |

| Time | % Mobile Phase A | % Mobile Phase B |
|---|---|---|
| 0 | 90.0 | 10.0 |
| 2 | 90.0 | 10.0 |
| 13 | 67.0 | 33.0 |
| 16 | 67.0 | 33.0 |
| 29 | 40.0 | 60.0 |
| 30 | 20.0 | 80.0 |
| 32 | 20.0 | 80.0 |
| 32 | 90.0 | 10.0 |
| 36 | 90.0 | 10.0 |

Total impurities (process-related and product-related) of the indacaterol forced degradation study samples are presented in Table 3. Forced degradation impurity peaks were identified based on their retention time relative (RRT) to the indacaterol peak. Impurity peaks already present in the indacaterol (control group at T0; total peak area approximately 2%) were considered process-related, while additional peaks formed after the degradation were considered product-related.

TABLE 3

Results of forced degradation experiments

| Sample | Timepoint | Indacaterol (%) | Total Impurities* (%) | Total Peak Area (%) |
|---|---|---|---|---|
| Control | T0 | 98.04 | 1.81 | 99.85 |
| Acidic Hydrolysis (1M HCl) | T0 | 95.81 | 4.01 | 99.82 |
| | 15 h | 92.54 | 7.25 | 99.79 |
| | Change in % peak | −3.27 | N/A | N/A |
| Basic Hydrolysis (1M NaOH) | T0 | 95.82 | 3.99 | 99.81 |
| | 15 h | 92.06 | 7.69 | 99.75 |
| | Change in % peak | −3.76 | N/A | N/A |
| Oxidation (1.2% $H_2O_2$) | 7 h | 97.03 | 2.77 | 99.89 |
| | 29 h | 90.76 | 8.83 | 99.59 |
| | Change in % peak | −6.27 | N/A | N/A |

*Includes 2% process-related impurity.

Percent total impurity in both 1 N HCl and 1 N NaOH samples stored for 15 hours at ambient temperature were the same (approximately 7% to 8%), while total impurities for the 1.2% $H_2O_2$ sample stored for 29 hours were approximately 9%. FIG. 1 shows the staggered chromatograms of the indacaterol forced degradation samples. The peak at the column void volume in the oxidized sample was attributed to water from the $H_2O_2$ solution and was excluded from the percent total impurities. Overall, the results indicate that the RP-HPLC method provides good separation of indacaterol impurities.

Example 2—Aqueous Solubility of Indacaterol

Solubility studies of indacaterol and indacaterol maleate were performed using an orbital shaker method. Excess indacaterol was placed in a glass vial with water. The initial pH of the water was 7.1. Samples were shaken for 12 hours to ensure equilibrium was reached. After the 12 hour period, the vial was removed from the shaker and allowed to settle for 30 minutes. Then, the sample was filtered using a 0.2 µM polyvinylidene fluoride (PVDF) syringe filter; the initial 0.5 mL of filtrate was discarded. The pH was then measured and the concentration of the indacaterol was evaluated by UV-Vis. Results are shown in Table 4.

TABLE 4

Maximum solubility of indacaterol and indacaterol maleate

| Chemical | Solubility (µg/mL) | pH after dissolution |
|---|---|---|
| Indacaterol maleate | 230 | 3.30 |
| Indacaterol | <1 µg/mL* | 6.20 |

*No detection. Lowest standard for UV spec is 1 µg/mL

Indacaterol was insoluble in water at pH 7.1. The change in pH for the sample is likely due to dissolved environmental $CO_2$. The pH of the indacaterol maleate solution is attributed primarily to the dissolution of the salt and formation of maleic acid and indacaterol free base.

Example 3—Aqueous Solubility of Indacaterol with Varying pH

Solubility studies of indacaterol in solutions of varying pH were performed using an orbital shaker method. Excess indacaterol was placed in a glass vial with an aqueous citrate buffer (5 mM; prepared from citric acid and NaOH). Samples were shaken for 12 to 24 hours to ensure equilibrium was reached before checking and adjusting the pH (using 1 M HCl and NaOH) and placing samples back into the orbital shaker for an additional 12 hours. This process was repeated up to two times or until the desired pH was obtained. After the desired pH was reached, the vial was removed from the shaker and allowed to settle for 30 minutes. Then, the sample was filtered using a 0.2 µM PVDF syringe filter; the initial 0.5 mL of filtrate was discarded. The pH was then measured and the concentration of the indacaterol was evaluated by UV-Vis. Results are shown in Table 5. Solubility of indacaterol was found to increase with decreasing pH.

TABLE 5

Indacaterol solubility in citrate buffer.

| Sample # | Solubility (µg/mL) | pH after dissolution |
|---|---|---|
| 3.1 | 647 | 3.66 |
| 3.2 | 399 | 4.02 |
| 3.3 | 290 | 4.42 |
| 3.4 | 122 | 5.08 |
| 3.5 | 10 | 6.22 |

Example 4—Aqueous Solubility of Indacaterol with Various Buffers

Solubility studies of indacaterol in solutions of varying pH and various buffers were performed using an orbital shaker method. Excess indacaterol was placed in a glass vial with water with the appropriate buffer and 300 mM mannitol. Samples were shaken for 12 to 24 hours to ensure equilibrium was reached before checking and adjusting the pH (using 1 M HCl and NaOH) and placing samples back into the orbital shaker for an additional 12 hours. This process was repeated up to two times or until the desired pH was obtained. After the desired pH was reached, the vial was removed from the shaker and allowed to settle for 30 minutes. Then, the sample was filtered using a 0.2 µM PVDF syringe filter; the initial 0.5 mL of filtrate was discarded. The pH was then measured and the concentration of the indacaterol was evaluated by UV-Vis. Results shown in Table 6.

TABLE 6

Effect of buffer species and pH on indacaterol solubility.

| Formulation | Buffer | pH | Solubility (µg/mL) | Avg. Solubility (µg/mL) |
|---|---|---|---|---|
| 4.1 | Acetate | 3.46 | 481 | — |
| 4.2 | | 4.11 | 325 | 335 |
| 4.3 | | 4.01 | 353 | |
| 4.4 | | 4.07 | 329 | |
| 4.5 | | 4.94 | 145 | — |
| 4.6 | Tartrate | 3.03 | 449 | — |

TABLE 6-continued

Effect of buffer species and pH on indacaterol solubility.

| Formulation | Buffer | pH | Solubility (µg/mL) | Avg. Solubility (µg/mL) |
|---|---|---|---|---|
| 4.7 | | 3.96 | 349 | 352 |
| 4.8 | | 4.00 | 347 | |
| 4.9 | | 3.99 | 359 | |
| 4.10 | | 4.94 | 178 | — |
| 4.11 | Citrate | 3.11 | 487 | — |
| 4.12 | | 3.99 | 370 | 342 |
| 4.13 | | 4.01 | 330 | |
| 4.14 | | 4.03 | 326 | |
| 4.15 | | 5.05 | 220 | — |

Example 5—Solubility of Indacaterol in Formulations with Tonicity Modifiers and Co-Solvents Solubility studies of indacaterol in solutions of varying pH and tonicity modifiers were performed using an orbital shaker method. Excess indacaterol was placed in a glass vial with water, 5 mM citrate, and various tonicity modifiers and/or co-solvents. Samples were shaken for 12 to 24 hours to ensure equilibrium was reached before checking and adjusting the pH (using 1 M HCl and NaOH) and placing samples back into the orbital shaker for an additional 12 hours. This process was repeated up to 2 times or until the desired pH was obtained. After the desired pH was reached, the vial was removed from the shaker and allowed to settle for 30 minutes. Then, the sample was filtered using a 0.2 µM PVDF syringe filter; the initial 0.5 mL of filtrate was discarded. The pH was then measured and the concentration of the indacaterol was evaluated by UV-Vis. Results shown in Table 7.

TABLE 7

Indacaterol solubility in solution with various tonicifiers and co-solvents

| Formulation | Excipients | pH | Solubility (µg/mL) | Avg. Solubility (µg/mL) |
|---|---|---|---|---|
| 5.1 | 300 mM mannitol | 3.99 | 330 | 342 |
| 5.2 | | 4.01 | 326 | |
| 5.3 | | 4.03 | 220 | |
| 5.4 | 5% v/v EtOH | 4.01 | 400 | — |
| 5.5 | 5% v/v EtOH + | 3.10 | 463 | — |
| 5.6 | 300 mM mannitol | 4.04 | 381 | 377 |
| 5.7 | | 4.05 | 384 | |
| 5.8 | | 4.00 | 366 | |
| 5.9 | | 4.97 | 292 | — |
| 5.10 | 5% v/v EtOH + | 2.97 | 180 | — |
| 5.11 | 150 mM NaCl | 3.97 | 176 | 178 |
| 5.12 | | 3.97 | 164 | |
| 5.13 | | 3.98 | 194 | |
| 5.14 | | 5.02 | 201 | — |

Example 6—Solubility of Indacaterol in Formulations Including a Cyclodextrin

Solubility studies of the impact of cyclodextrin on aqueous solutions of indacaterol were performed using an orbital shaker method (Formulations 6.1-6.11). Excess indacaterol was placed in a glass vial with water, 5 mM citrate, mannitol or NaCl, and sulfobutyl ether β-cyclodextrin (SBE-β-CD). Samples were shaken for 12 to 24 hours to ensure equilibrium was reached before checking and adjusting the pH (using 1 M HCl and NaOH) and placing samples back into the orbital shaker for an additional 12 hours. This process was repeated up to 2 times or until the desired pH was obtained. After the desired pH was reached, the vial was removed from the shaker and allowed to settle for 30 minutes. Then, the sample was filtered using a 0.2 µM PVDF syringe filter; the initial 0.5 mL of filtrate was discarded. The pH was then measured and the concentration of the indacaterol was evaluated by UV-Vis. Results shown in Table 8.

For examples 6.12 and 6.13, excess indacaterol was placed in a glass vial with water, 5 mM citrate and sulfobutyl ether β-cyclodextrin (SBE-β-CD). Samples were stirred at 250 rpm up to 24 hours to ensure equilibrium. The vial was removed from the shaker and allowed to settle for approximately 24 hours. Then, the sample was filtered using a 0.2 µM PVDF syringe filter; the initial 0.5 mL of filtrate was discarded. The pH was then measured and the concentration of the indacaterol was evaluated by UV-Vis. Results shown in Table 8.

TABLE 8

Indacaterol solubility in formulations with SBE-β-CD.

| Formulation | Excipients | pH | Solubility (µg/mL) | Avg. Solubility (µg/mL) |
|---|---|---|---|---|
| 6.1 | 0.5% w/v SBE-β-CD + | 3.16 | 1163 | — |
| 6.2 | 300 mM mannitol | 4.04 | 1113 | 1135 |
| 6.3 | | 4.05 | 1167 | |
| 6.4 | | 3.98 | 1125 | |
| 6.5 | | 5.27 | 1026 | — |
| 6.6 | 0.25% w/v SBE-β-CD + | 3.13 | 644 | — |
| 6.7 | 300 mM mannitol | 4.08 | 627 | — |
| 6.8 | | 5.26 | 587 | — |
| 6.9 | 0.5% w/v SBE-β-CD + | 4.06 | 1178 | 1148 |
| 6.10 | 150 mM NaCl | 4.05 | 1152 | |
| 6.11 | | 4.05 | 1113 | |
| 6.12 | 5% w/v SBE-β-CD | 5.18 | 1480.4 | — |
| 6.13 | 10% w/v SBE-β-CD | 5.35 | 1546.4 | — |

Example 7—Stability Studies of Liquid Indacaterol Formulations

A series of formulations of indacaterol were prepared for the stability study. Each formulation was transferred to a glass bottle, then excess indacaterol was added. The bottles were capped, placed horizontally on an orbital shaker set to 200 rpm overnight. The following day, the pH of each formulation was measured and subsequently adjusted with 1 N NaOH and/or 1 N HCl to maintain target pH. Bottles were placed back onto the shaker overnight. The bottles were then removed from the shaker and checked to ensure that the pH was stable. Each formulation was filtered through a PVDF filter membrane to remove excess indacaterol and diluted to 75% concentration using the corresponding formulation buffer. The pH of each formulation was measured and pH adjusted with 1 M NaOH and/or 1 M HCl to maintain target pH. Finally, each formulation was filtered through a PVDF filter membrane to minimize particulate load and transferred to a biosafety cabinet (BSC) for vial filling. The osmolality and viscosity of the formulations were tested (see Table 9). Indacaterol concentration was determined by RP-HPLC.

TABLE 9

Liquid formulations of indacaterol for stability studies.

| Name | Buffer | pH | Excipients | Indacaterol concentration (μg/mL) | Osmolality (mOsm/kg) | Viscosity (cP) |
|---|---|---|---|---|---|---|
| F2 | Citrate | 3.0 | 290 mM mannitol | 222 | 407 | 1.2 |
| F3 | 50 mM | 4.0 | | 198 | 387 | 1.16 |
| F4 | | 3.0 | 290 mM mannitol | 212 | 1300 | 1.33 |
| F5 | | 4.0 | 5% w/v ethanol | 226 | 1314 | 1.32 |
| F6 | | 3.0 | 290 mM mannitol | 800 | 416 | 1.15 |
| F7 | | 4.0 | 0.5% w/v SBE-β-CD | 793 | 407 | 1.19 |
| F8 | | 3.0 | 145 mM NaCl | 703 | 390 | 1.03 |
| F9 | | 4.0 | 0.5% w/v SBE-β-CD | 733 | 360 | 1.04 |

Figure 2A:
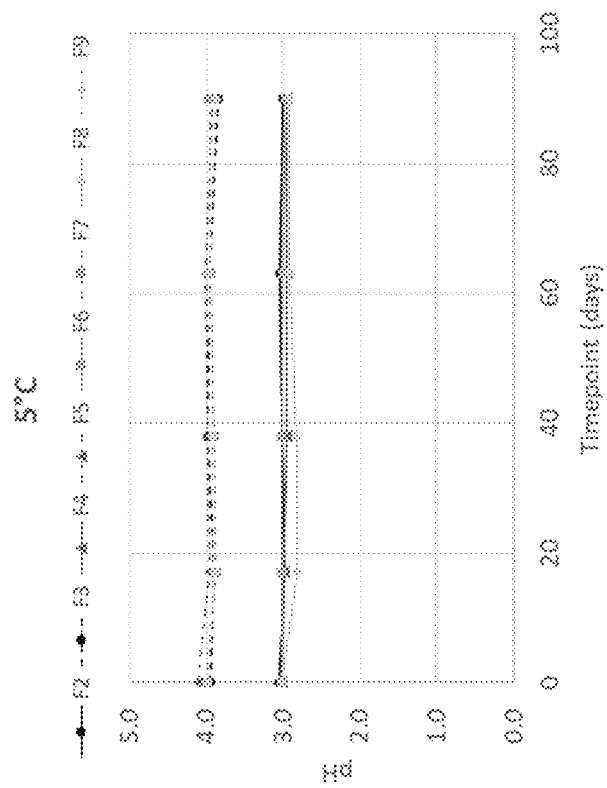
Figure 2B:
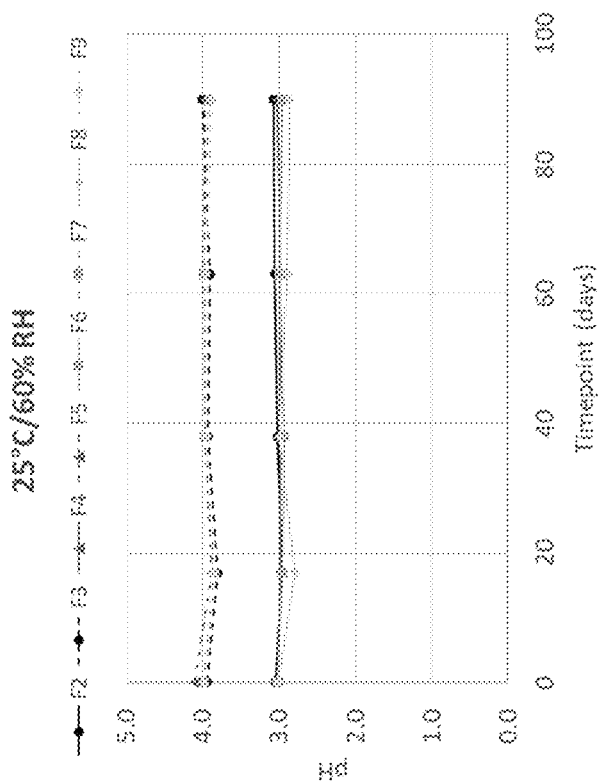
Figure 2C:
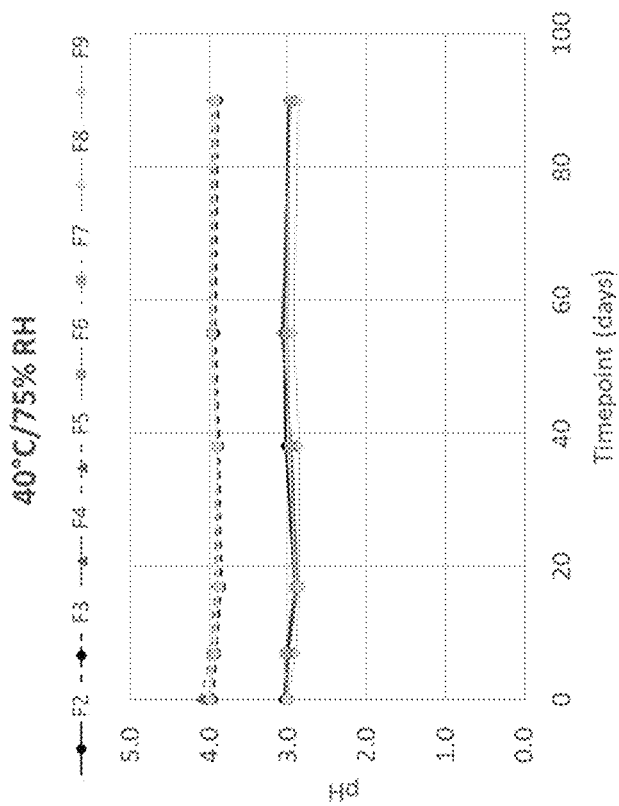
Figure 3A:
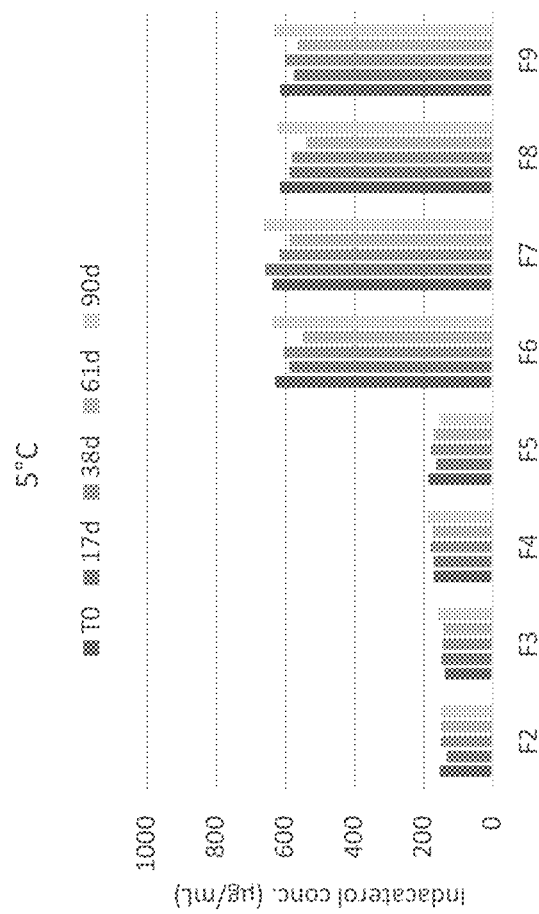
Figure 3B:
Figure 3C:
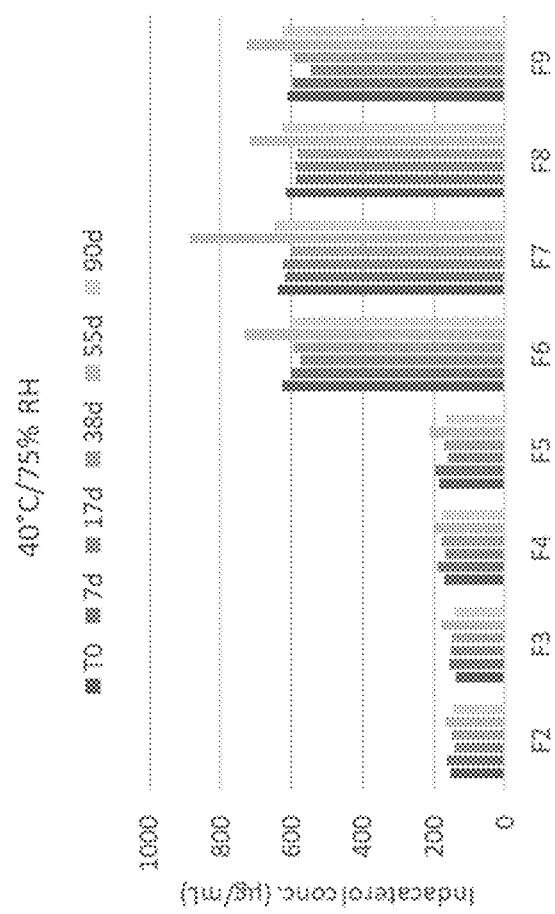
Figure 4:
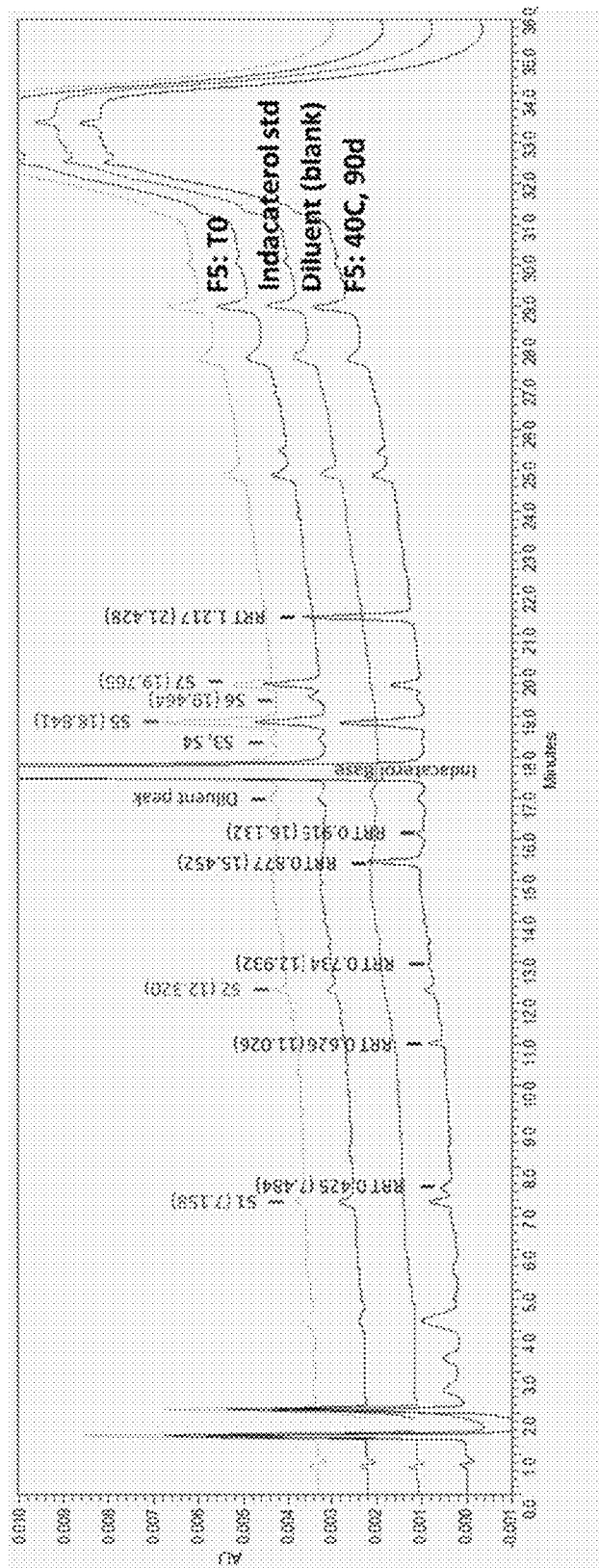
Figure 5:
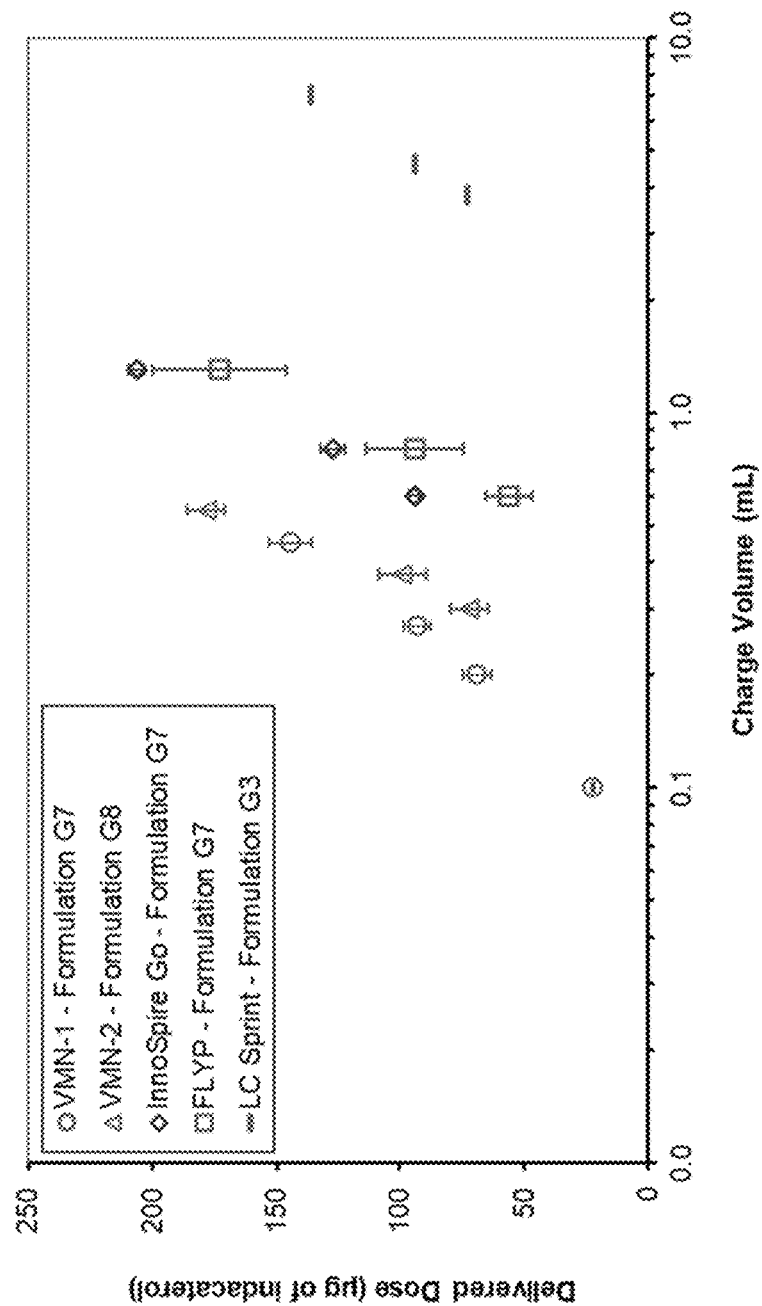
Figure 6:
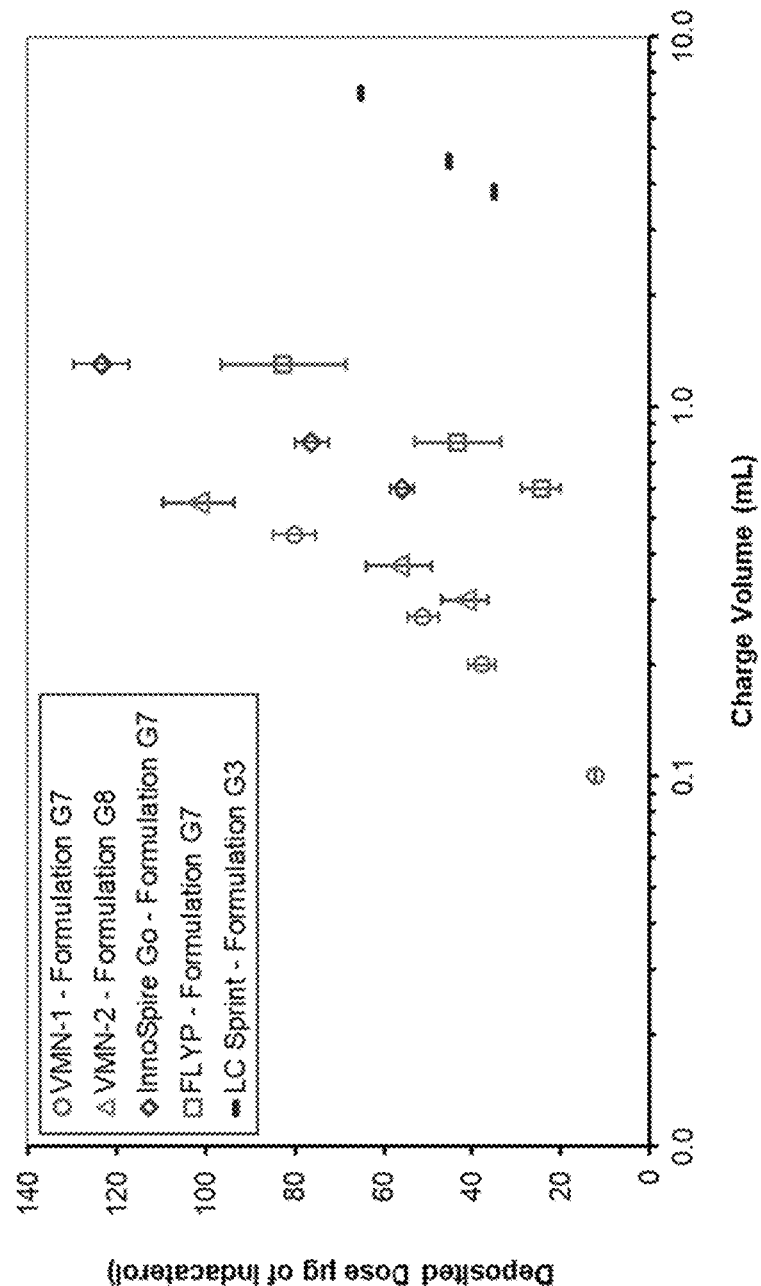

The formulations were stored under various conditions and the pH and concentration were tested at various time points to evaluate the stability of the formulations. For all formulations, the pH remained relatively unchanged over a 90-day period. FIG. 2 shows the data for all formulations stored under various conditions. For all formulations, the concentration of indacaterol remained relatively unchanged over a 90-day period. FIG. 3 shows the indacaterol concentration under all storage conditions for each formulation. For all formulations, product-related impurities were identified at relative retention times of approximately 0.425, 0.626, 0.734, 0.877, 0.915, and 1.217 (see FIG. 4). A summary of the percentage change (90 d vs T0) in indacaterol main peak and total product-related impurities is shown in Table 10.

TABLE 10

Summary of % change (90 d vs T0) in indacaterol main peak and total product-related impurities for indacaterol liquid formulations stored at various conditions.

| | | | | % Change of Indacaterol content (90 d vs Time 0) | | | | | |
|---|---|---|---|---|---|---|---|---|---|
| | | | | 40° C./75% RH | | 25° C./60% RH | | 5° C. | |
| Formulation | | | | Indacaterol | Product-related | Indacaterol | Product-related | Indacaterol | Product-related |
| Name | Buffer | Excipients | pH | Main Peak | impurities | Main Peak | impurities | Main Peak | impurities |
| F2 | 50 mM Citrate | 290 mM mannitol | 3.0 | −1.00 | 0.69 | −0.70 | 0.13 | −0.46 | 0.00 |
| F3 | | | 4.0 | −1.35 | 1.12 | −0.38 | 0.15 | −0.26 | 0.00 |
| F4 | | 290 mM mannitol 5% w/v ethanol | 3.0 | −1.83 | 1.67 | −0.88 | 0.50 | −0.28 | 0.00 |
| F5 | | | 4.0 | −3.04 | 2.53 | −0.91 | 0.40 | −0.36 | 0.00 |
| F6 | | 290 mM mannitol 0.5% w/v SBE-β-CD | 3.0 | −0.64 | 0.63 | −0.45 | 0.23 | −0.30 | 0.00 |
| F7 | | | 4.0 | −0.73 | 0.66 | −0.38 | 0.21 | 0.06 | 0.00 |
| F8 | | 145 mM NaCl 0.5% w/v SBE-β-CD | 3.0 | −0.15 | 0.00 | 0.03 | 0.00 | 0.05 | 0.00 |
| F9 | | | 4.0 | −0.05 | 0.11 | −0.02 | 0.00 | −0.10 | 0.00 |

The full impurities data for stability samples stored for up to 90 days at 40° C., 25° C., and 5° C. are presented in Tables 11-13.

TABLE 11

% main peak impurities for indacaterol liquid formulations stored at 40° C./75% RH for 90 days.

| Formulation | Timepoint (days) | Indacaterol main peak % Indacaterol | Product-related impurities (% total excludes process-related impurities and diluent peak) | | | | | | | | Process and product-related impurities (% total excludes diluent peak) | |
|---|---|---|---|---|---|---|---|---|---|---|---|---|
| | | | RRT* ~0.425 | RRT ~0.626 | RRT ~0.734 | RRT ~0.877 | RRT ~0.915 | RRT ~1.217 | % Total Impurities | % Total area | % Total Impurities | % Total area |
| F2 | 0 | 98.10 | 0.00 | 0.00 | 0.00 | 0.00 | 0.00 | 0.00 | 0.00 | 98.10 | 1.80 | 99.90 |
| | 7 | 98.19 | 0.00 | 0.00 | 0.00 | 0.00 | 0.00 | 0.00 | 0.00 | 98.19 | 1.64 | 99.83 |
| | 17 | 96.54 | 0.00 | 0.00 | 0.00 | 0.80 | 0.00 | 0.00 | 0.80 | 97.34 | 3.20 | 99.74 |
| | 38 | 97.36 | 0.00 | 0.00 | 0.00 | 0.44 | 0.00 | 0.00 | 0.44 | 97.80 | 2.47 | 99.83 |
| | 55 | 97.63 | 0.00 | 0.00 | 0.00 | 0.42 | 0.00 | 0.00 | 0.42 | 98.05 | 2.16 | 99.79 |

TABLE 11-continued

% main peak impurities for indacaterol liquid formulations stored at 40° C./75% RH for 90 days.

| Formulation | Timepoint (days) | Indacaterol main peak % Indacaterol | Product-related impurities (% total excludes process-related impurities and diluent peak) | | | | | | | % Total area | Process and product-related impurities (% total excludes diluent peak) | |
|---|---|---|---|---|---|---|---|---|---|---|---|---|
| | | | RRT* ~0.425 | RRT ~0.626 | RRT ~0.734 | RRT ~0.877 | RRT ~0.915 | RRT ~1.217 | % Total Impurities | | % Total Impurities | % Total area |
| | 90 | 97.10 | 0.00 | 0.00 | 0.00 | 0.69 | 0.00 | 0.00 | 0.69 | 97.79 | 2.74 | 99.84 |
| | Change peak % in 90 d | −1.00 | 0.00 | 0.00 | 0.00 | 0.69 | 0.00 | 0.00 | 0.69 | | | |
| F3 | 0 | 97.85 | 0.00 | 0.00 | 0.00 | 0.00 | 0.00 | 0.00 | 0.00 | 97.85 | 2.03 | 99.88 |
| | 7 | 97.93 | 0.00 | 0.00 | 0.00 | 0.12 | 0.00 | 0.00 | 0.12 | 98.05 | 1.91 | 99.84 |
| | 17 | 97.08 | 0.00 | 0.00 | 0.00 | 0.16 | 0.00 | 0.00 | 0.16 | 97.24 | 2.67 | 99.75 |
| | 38 | 96.84 | 0.00 | 0.00 | 0.00 | 0.57 | 0.00 | 0.00 | 0.57 | 97.41 | 2.98 | 99.82 |
| | 55 | 97.41 | 0.00 | 0.00 | 0.00 | 0.43 | 0.00 | 0.00 | 0.43 | 97.84 | 2.37 | 99.78 |
| | 90 | 96.50 | 0.19 | 0.09 | 0.00 | 0.77 | 0.07 | 0.00 | 1.12 | 97.62 | 3.33 | 99.83 |
| | Change peak % in 90 d | −1.35 | 0.19 | 0.09 | 0.00 | 0.77 | 0.07 | 0.00 | 1.12 | | | |
| F4 | 0 | 98.00 | 0.00 | 0.00 | 0.00 | 0.00 | 0.00 | 0.00 | 0.00 | 98.00 | 1.91 | 99.91 |
| | 7 | 98.02 | 0.00 | 0.00 | 0.00 | 0.00 | 0.00 | 0.10 | 0.10 | 98.12 | 1.84 | 99.86 |
| | 17 | 97.22 | 0.00 | 0.00 | 0.00 | 0.14 | 0.00 | 0.26 | 0.40 | 97.62 | 2.57 | 99.79 |
| | 38 | 97.29 | 0.00 | 0.00 | 0.00 | 0.29 | 0.00 | 0.52 | 0.81 | 98.10 | 2.55 | 99.84 |
| | 55 | 97.07 | 0.00 | 0.00 | 0.00 | 0.31 | 0.00 | 0.72 | 1.03 | 98.10 | 2.77 | 99.84 |
| | 90 | 96.17 | 0.00 | 0.00 | 0.00 | 0.47 | 0.00 | 1.20 | 1.67 | 97.84 | 3.70 | 99.87 |
| | Change peak % in 90 d | −1.83 | 0.00 | 0.00 | 0.00 | 0.47 | 0.00 | 1.20 | 1.67 | | | |
| F5 | 0 | 98.13 | 0.00 | 0.00 | 0.00 | 0.00 | 0.00 | 0.00 | 0.00 | 98.13 | 1.78 | 99.91 |
| | 7 | 98.05 | 0.00 | 0.00 | 0.00 | 0.00 | 0.00 | 0.11 | 0.11 | 98.16 | 1.85 | 99.90 |
| | 17 | 96.89 | 0.00 | 0.00 | 0.00 | 0.18 | 0.00 | 0.28 | 0.46 | 97.35 | 2.88 | 99.77 |
| | 38 | 96.89 | 0.00 | 0.00 | 0.00 | 0.43 | 0.00 | 0.57 | 1.00 | 97.89 | 2.97 | 99.86 |
| | 55 | 96.70 | 0.00 | 0.00 | 0.00 | 0.39 | 0.00 | 0.78 | 1.17 | 97.87 | 3.11 | 99.81 |
| | 90 | 95.09 | 0.20 | 0.13 | 0.17 | 0.65 | 0.12 | 1.26 | 2.53 | 97.62 | 4.78 | 99.87 |
| | Δ peak % in 90 d | −3.04 | 0.20 | 0.13 | 0.17 | 0.65 | 0.12 | 1.26 | 2.53 | | | |
| F6 | 0 | 98.12 | 0.00 | 0.00 | 0.00 | 0.00 | 0.00 | 0.00 | 0.00 | 98.12 | 1.75 | 99.87 |
| | 7 | 98.22 | 0.00 | 0.00 | 0.00 | 0.00 | 0.00 | 0.00 | 0.00 | 98.22 | 1.64 | 99.86 |
| | 17 | 97.72 | 0.00 | 0.00 | 0.00 | 0.15 | 0.00 | 0.00 | 0.15 | 97.87 | 2.02 | 99.74 |
| | 38 | 97.82 | 0.00 | 0.00 | 0.00 | 0.30 | 0.00 | 0.00 | 0.30 | 98.12 | 2.04 | 99.86 |
| | 55 | 97.48 | 0.00 | 0.00 | 0.00 | 0.50 | 0.00 | 0.00 | 0.50 | 97.98 | 2.34 | 99.82 |
| | 90 | 97.48 | 0.00 | 0.00 | 0.00 | 0.63 | 0.00 | 0.00 | 0.63 | 98.11 | 2.40 | 99.88 |
| | Change peak % in 90 d | −0.64 | 0.00 | 0.00 | 0.00 | 0.63 | 0.00 | 0.00 | 0.63 | | | |
| F7 | 0 | 97.99 | 0.00 | 0.00 | 0.00 | 0.00 | 0.00 | 0.00 | 0.00 | 97.99 | 1.88 | 99.87 |
| | 7 | 98.22 | 0.00 | 0.00 | 0.00 | 0.00 | 0.00 | 0.00 | 0.00 | 98.22 | 1.64 | 99.86 |
| | 17 | 97.82 | 0.00 | 0.00 | 0.00 | 0.14 | 0.00 | 0.00 | 0.14 | 97.96 | 1.96 | 99.78 |
| | 38 | 97.83 | 0.00 | 0.00 | 0.00 | 0.25 | 0.00 | 0.00 | 0.25 | 98.08 | 2.02 | 99.85 |
| | 55 | 97.66 | 0.00 | 0.00 | 0.00 | 0.33 | 0.00 | 0.00 | 0.33 | 97.99 | 2.16 | 99.82 |
| | 90 | 97.26 | 0.00 | 0.09 | 0.00 | 0.57 | 0.00 | 0.00 | 0.66 | 97.92 | 2.62 | 99.88 |
| | Change peak % in 90 d | −0.73 | 0.00 | 0.09 | 0.00 | 0.57 | 0.00 | 0.00 | 0.66 | | | |
| F8 | 0 | 97.98 | 0.00 | 0.00 | 0.00 | 0.00 | 0.00 | 0.00 | 0.00 | 97.98 | 1.90 | 99.88 |
| | 7 | 98.08 | 0.00 | 0.00 | 0.00 | 0.00 | 0.00 | 0.00 | 0.00 | 98.08 | 1.77 | 99.85 |
| | 17 | 97.94 | 0.00 | 0.00 | 0.00 | 0.00 | 0.00 | 0.00 | 0.00 | 97.94 | 1.84 | 99.78 |
| | 38 | 98.06 | 0.00 | 0.00 | 0.00 | 0.00 | 0.00 | 0.00 | 0.00 | 98.06 | 1.79 | 99.85 |
| | 55 | 98.01 | 0.00 | 0.00 | 0.00 | 0.00 | 0.00 | 0.00 | 0.00 | 98.01 | 1.79 | 99.80 |
| | 90 | 97.83 | 0.00 | 0.00 | 0.00 | 0.00 | 0.00 | 0.00 | 0.00 | 97.83 | 2.04 | 99.87 |
| | Change peak % in 90 d | −0.15 | 0.00 | 0.00 | 0.00 | 0.00 | 0.00 | 0.00 | 0.00 | | | |
| F9 | 0 | 97.93 | 0.00 | 0.00 | 0.00 | 0.00 | 0.00 | 0.00 | 0.00 | 97.93 | 1.94 | 99.87 |
| | 7 | 98.20 | 0.00 | 0.00 | 0.00 | 0.00 | 0.00 | 0.00 | 0.00 | 98.20 | 1.80 | 100.00 |
| | 17 | 97.96 | 0.00 | 0.00 | 0.00 | 0.00 | 0.00 | 0.00 | 0.00 | 97.96 | 1.81 | 99.77 |
| | 38 | 97.98 | 0.00 | 0.00 | 0.00 | 0.00 | 0.00 | 0.00 | 0.00 | 97.98 | 1.85 | 99.84 |
| | 55 | 97.88 | 0.00 | 0.07 | 0.00 | 0.00 | 0.00 | 0.00 | 0.07 | 97.95 | 1.93 | 99.81 |
| | 90 | 97.88 | 0.00 | 0.11 | 0.00 | 0.00 | 0.00 | 0.00 | 0.11 | 97.99 | 1.99 | 99.87 |
| | Change peak % in 90 d | −0.05 | 0.00 | 0.11 | 0.00 | 0.00 | 0.00 | 0.00 | 0.11 | | | |

TABLE 12

% main peak impurities for indacaterol liquid formulations stored at 25° C./60% RH for 90 days.

| Formulation | Timepoint (days) | Indacaterol main peak % Indacaterol | Product-related impurities (% total excludes process-related impurities and diluent peak) | | | | | | | % Total area | Process and product-related impurities (% total excludes diluent peak) | |
|---|---|---|---|---|---|---|---|---|---|---|---|---|
| | | | RRT ~0.425 | RRT ~0.626 | RRT ~0.734 | RRT ~0.877 | RRT ~0.915 | RRT ~1.217 | % Total Impurities | | % Total Impurities | % Total area |
| F2 | 0 | 98.10 | 0.00 | 0.00 | 0.00 | 0.00 | 0.00 | 0.00 | 0.00 | 98.10 | 1.80 | 99.90 |
| | 17 | 97.73 | 0.00 | 0.00 | 0.00 | 0.00 | 0.00 | 0.00 | 0.00 | 97.73 | 2.00 | 99.73 |
| | 38 | 98.07 | 0.00 | 0.00 | 0.00 | 0.00 | 0.00 | 0.00 | 0.00 | 98.07 | 1.77 | 99.84 |
| | 63 | 97.90 | 0.00 | 0.00 | 0.00 | 0.11 | 0.00 | 0.00 | 0.11 | 98.01 | 1.91 | 99.81 |
| | 90 | 97.40 | 0.00 | 0.00 | 0.00 | 0.13 | 0.00 | 0.00 | 0.13 | 97.53 | 2.45 | 99.85 |
| | Δ peak % in 90 d | −0.70 | 0.00 | 0.00 | 0.00 | 0.13 | 0.00 | 0.00 | 0.13 | | | |
| F3 | 0 | 97.85 | 0.00 | 0.00 | 0.00 | 0.00 | 0.00 | 0.00 | 0.00 | 97.85 | 2.03 | 99.88 |
| | 17 | 97.42 | 0.00 | 0.00 | 0.00 | 0.00 | 0.00 | 0.00 | 0.00 | 97.42 | 2.34 | 99.76 |
| | 38 | 97.94 | 0.00 | 0.00 | 0.00 | 0.09 | 0.00 | 0.00 | 0.09 | 98.03 | 1.89 | 99.83 |
| | 63 | 97.80 | 0.00 | 0.00 | 0.00 | 0.14 | 0.00 | 0.00 | 0.14 | 97.94 | 1.99 | 99.79 |
| | 90 | 97.47 | 0.00 | 0.00 | 0.00 | 0.15 | 0.00 | 0.00 | 0.15 | 97.62 | 2.38 | 99.85 |
| | Δ peak % in 90 d | −0.38 | 0.00 | 0.00 | 0.00 | 0.15 | 0.00 | 0.00 | 0.15 | | | |
| F4 | 0 | 98.00 | 0.00 | 0.00 | 0.00 | 0.00 | 0.00 | 0.00 | 0.00 | 98.00 | 1.91 | 99.91 |
| | 17 | 97.44 | 0.00 | 0.00 | 0.00 | 0.00 | 0.00 | 0.00 | 0.00 | 97.44 | 2.32 | 99.76 |
| | 38 | 97.85 | 0.00 | 0.00 | 0.00 | 0.09 | 0.00 | 0.12 | 0.21 | 98.06 | 1.99 | 99.84 |
| | 63 | 97.73 | 0.00 | 0.00 | 0.00 | 0.14 | 0.00 | 0.19 | 0.33 | 98.06 | 2.10 | 99.83 |
| | 90 | 97.12 | 0.00 | 0.00 | 0.00 | 0.27 | 0.00 | 0.23 | 0.50 | 97.62 | 2.75 | 99.87 |
| | Δ peak % in 90 d | −0.88 | 0.00 | 0.00 | 0.00 | 0.27 | 0.00 | 0.23 | 0.50 | | | |
| F5 | 0 | 98.13 | 0.00 | 0.00 | 0.00 | 0.00 | 0.00 | 0.00 | 0.00 | 98.13 | 1.78 | 99.91 |
| | 17 | 97.46 | 0.00 | 0.00 | 0.00 | 0.00 | 0.00 | 0.00 | 0.00 | 97.46 | 2.32 | 99.78 |
| | 38 | 97.84 | 0.00 | 0.00 | 0.00 | 0.09 | 0.00 | 0.13 | 0.22 | 98.06 | 2.01 | 99.85 |
| | 63 | 97.71 | 0.00 | 0.00 | 0.00 | 0.14 | 0.00 | 0.23 | 0.37 | 98.08 | 2.10 | 99.81 |
| | 90 | 97.22 | 0.00 | 0.00 | 0.00 | 0.13 | 0.00 | 0.27 | 0.40 | 97.62 | 2.67 | 99.89 |
| | Δ peak % in 90 d | −0.91 | 0.00 | 0.00 | 0.00 | 0.13 | 0.00 | 0.27 | 0.40 | | | |
| F6 | 0 | 98.12 | 0.00 | 0.00 | 0.00 | 0.00 | 0.00 | 0.00 | 0.00 | 98.12 | 1.75 | 99.87 |
| | 17 | 98.02 | 0.00 | 0.00 | 0.00 | 0.00 | 0.00 | 0.00 | 0.00 | 98.02 | 1.78 | 99.80 |
| | 38 | 98.35 | 0.00 | 0.00 | 0.00 | 0.00 | 0.00 | 0.00 | 0.00 | 98.35 | 1.65 | 100.00 |
| | 63 | 97.87 | 0.00 | 0.00 | 0.00 | 0.14 | 0.00 | 0.00 | 0.14 | 98.01 | 1.96 | 99.83 |
| | 90 | 97.67 | 0.00 | 0.00 | 0.00 | 0.23 | 0.00 | 0.00 | 0.23 | 97.90 | 2.21 | 99.88 |
| | Δ peak % in 90 d | −0.45 | 0.00 | 0.00 | 0.00 | 0.23 | 0.00 | 0.00 | 0.23 | | | |
| F7 | 0 | 97.99 | 0.00 | 0.00 | 0.00 | 0.00 | 0.00 | 0.00 | 0.00 | 97.99 | 1.88 | 99.87 |
| | 17 | 97.96 | 0.00 | 0.00 | 0.00 | 0.00 | 0.00 | 0.00 | 0.00 | 97.96 | 1.85 | 99.81 |
| | 38 | 98.06 | 0.00 | 0.00 | 0.00 | 0.00 | 0.00 | 0.00 | 0.00 | 98.06 | 1.78 | 99.84 |
| | 63 | 97.96 | 0.00 | 0.00 | 0.00 | 0.08 | 0.00 | 0.00 | 0.08 | 98.04 | 1.85 | 99.81 |
| | 90 | 97.61 | 0.00 | 0.00 | 0.08 | 0.13 | 0.00 | 0.00 | 0.21 | 97.82 | 2.24 | 99.85 |
| | Δ peak % in 90 d | −0.38 | 0.00 | 0.00 | 0.08 | 0.13 | 0.00 | 0.00 | 0.21 | | | |
| F8 | 0 | 97.98 | 0.00 | 0.00 | 0.00 | 0.00 | 0.00 | 0.00 | 0.00 | 97.98 | 1.90 | 99.88 |
| | 17 | 97.86 | 0.00 | 0.00 | 0.00 | 0.00 | 0.00 | 0.00 | 0.00 | 97.86 | 1.89 | 99.75 |
| | 38 | 97.57 | 0.00 | 0.00 | 0.00 | 0.00 | 0.00 | 0.00 | 0.00 | 97.57 | 2.33 | 99.90 |
| | 63 | 98.01 | 0.00 | 0.00 | 0.00 | 0.00 | 0.00 | 0.00 | 0.00 | 98.01 | 1.80 | 99.81 |
| | 90 | 98.01 | 0.00 | 0.00 | 0.00 | 0.00 | 0.00 | 0.00 | 0.00 | 98.01 | 1.86 | 99.87 |
| | Δ peak % in 90 d | 0.03 | 0.00 | 0.00 | 0.00 | 0.00 | 0.00 | 0.00 | 0.00 | | | |
| F9 | 0 | 97.93 | 0.00 | 0.00 | 0.00 | 0.00 | 0.00 | 0.00 | 0.00 | 97.93 | 1.94 | 99.87 |
| | 17 | 97.94 | 0.00 | 0.00 | 0.00 | 0.00 | 0.00 | 0.00 | 0.00 | 97.94 | 1.83 | 99.77 |
| | 38 | 98.03 | 0.00 | 0.00 | 0.00 | 0.00 | 0.00 | 0.00 | 0.00 | 98.03 | 1.81 | 99.84 |
| | 63 | 97.94 | 0.00 | 0.00 | 0.00 | 0.00 | 0.00 | 0.00 | 0.00 | 97.94 | 1.87 | 99.81 |
| | 90 | 97.91 | 0.00 | 0.00 | 0.00 | 0.00 | 0.00 | 0.00 | 0.00 | 97.91 | 1.97 | 99.88 |
| | Δ peak % in 90 d | −0.02 | 0.00 | 0.00 | 0.00 | 0.00 | 0.00 | 0.00 | 0.00 | | | |

*RRT = relative retention time

TABLE 13

% main peak and impurities for indacaterol liquid formulations stored at 5° C. for 90 days.

| Formulation | Timepoint (days) | Indacaterol main peak % Indacaterol | Product-related impurities (% total excludes process-related impurities and diluent peak) | | | | | | | | Process and product-related impurities (% total excludes diluent peak) | |
|---|---|---|---|---|---|---|---|---|---|---|---|---|
| | | | RRT ~0.425 | RRT ~0.626 | RRT ~0.734 | RRT ~0.877 | RRT ~0.915 | RRT ~1.217 | % Total Impurities | % Total area | % Total Impurities | % Total area |
| F2 | 0 | 98.10 | 0.00 | 0.00 | 0.00 | 0.00 | 0.00 | 0.00 | 0.00 | 98.10 | 1.80 | 99.90 |
| | 17 | 97.89 | 0.00 | 0.00 | 0.00 | 0.00 | 0.00 | 0.00 | 0.00 | 97.89 | 1.79 | 99.68 |
| | 38 | 98.16 | 0.00 | 0.00 | 0.00 | 0.00 | 0.00 | 0.00 | 0.00 | 98.16 | 1.67 | 99.83 |
| | 63 | 98.01 | 0.00 | 0.00 | 0.00 | 0.00 | 0.00 | 0.00 | 0.00 | 98.01 | 1.77 | 99.78 |
| | 90 | 97.64 | 0.00 | 0.00 | 0.00 | 0.00 | 0.00 | 0.00 | 0.00 | 97.64 | 2.22 | 99.86 |
| | Δ peak % in 90 d | −0.46 | 0.00 | 0.00 | 0.00 | 0.00 | 0.00 | 0.00 | 0.00 | | | |
| F3 | 0 | 97.85 | 0.00 | 0.00 | 0.00 | 0.00 | 0.00 | 0.00 | 0.00 | 97.85 | 2.03 | 99.88 |
| | 17 | 97.66 | 0.00 | 0.00 | 0.00 | 0.00 | 0.00 | 0.00 | 0.00 | 97.66 | 2.06 | 99.72 |
| | 38 | 98.18 | 0.00 | 0.00 | 0.00 | 0.00 | 0.00 | 0.00 | 0.00 | 98.18 | 1.65 | 99.83 |
| | 63 | 97.98 | 0.00 | 0.00 | 0.00 | 0.00 | 0.00 | 0.00 | 0.00 | 97.98 | 1.83 | 99.81 |
| | 90 | 97.59 | 0.00 | 0.00 | 0.00 | 0.00 | 0.00 | 0.00 | 0.00 | 97.59 | 2.25 | 99.84 |
| | Δ peak % in 90 d | −0.26 | 0.00 | 0.00 | 0.00 | 0.00 | 0.00 | 0.00 | 0.00 | | | |
| F4 | 0 | 98.00 | 0.00 | 0.00 | 0.00 | 0.00 | 0.00 | 0.00 | 0.00 | 98.00 | 1.91 | 99.91 |
| | 17 | 97.59 | 0.00 | 0.00 | 0.00 | 0.00 | 0.00 | 0.00 | 0.00 | 97.59 | 2.17 | 99.76 |
| | 38 | 98.13 | 0.00 | 0.00 | 0.00 | 0.00 | 0.00 | 0.00 | 0.00 | 98.13 | 1.75 | 99.88 |
| | 63 | 98.05 | 0.00 | 0.00 | 0.00 | 0.00 | 0.00 | 0.00 | 0.00 | 98.05 | 1.79 | 99.84 |
| | 90 | 97.72 | 0.00 | 0.00 | 0.00 | 0.00 | 0.00 | 0.00 | 0.00 | 97.72 | 2.15 | 99.87 |
| | Δ peak % in 90 d | −0.28 | 0.00 | 0.00 | 0.00 | 0.00 | 0.00 | 0.00 | 0.00 | | | |
| F5 | 0 | 98.13 | 0.00 | 0.00 | 0.00 | 0.00 | 0.00 | 0.00 | 0.00 | 98.13 | 1.78 | 99.91 |
| | 17 | 97.60 | 0.00 | 0.00 | 0.00 | 0.00 | 0.00 | 0.00 | 0.00 | 97.60 | 2.17 | 99.77 |
| | 38 | 98.13 | 0.00 | 0.00 | 0.00 | 0.00 | 0.00 | 0.00 | 0.00 | 98.13 | 1.73 | 99.86 |
| | 63 | 98.05 | 0.00 | 0.00 | 0.00 | 0.00 | 0.00 | 0.00 | 0.00 | 98.05 | 1.64 | 99.69 |
| | 90 | 97.77 | 0.00 | 0.00 | 0.00 | 0.00 | 0.00 | 0.00 | 0.00 | 97.77 | 2.08 | 99.85 |
| | Δ peak % in 90 d | −0.36 | 0.00 | 0.00 | 0.00 | 0.00 | 0.00 | 0.00 | 0.00 | | | |
| F6 | 0 | 98.12 | 0.00 | 0.00 | 0.00 | 0.00 | 0.00 | 0.00 | 0.00 | 98.12 | 1.75 | 99.87 |
| | 17 | 98.07 | 0.00 | 0.00 | 0.00 | 0.00 | 0.00 | 0.00 | 0.00 | 98.07 | 1.70 | 99.77 |
| | 38 | 98.33 | 0.00 | 0.00 | 0.00 | 0.00 | 0.00 | 0.00 | 0.00 | 98.33 | 1.52 | 99.85 |
| | 63 | 97.99 | 0.00 | 0.00 | 0.00 | 0.00 | 0.00 | 0.00 | 0.00 | 97.99 | 1.84 | 99.83 |
| | 90 | 97.82 | 0.00 | 0.00 | 0.00 | 0.00 | 0.00 | 0.00 | 0.00 | 97.82 | 2.06 | 99.88 |
| | Δ peak % in 90 d | −0.30 | 0.00 | 0.00 | 0.00 | 0.00 | 0.00 | 0.00 | 0.00 | | | |
| F7 | 0 | 97.99 | 0.00 | 0.00 | 0.00 | 0.00 | 0.00 | 0.00 | 0.00 | 97.99 | 1.88 | 99.87 |
| | 17 | 98.06 | 0.00 | 0.00 | 0.00 | 0.00 | 0.00 | 0.00 | 0.00 | 98.06 | 1.75 | 99.81 |
| | 38 | 98.39 | 0.00 | 0.00 | 0.00 | 0.00 | 0.00 | 0.00 | 0.00 | 98.39 | 1.61 | 100.00 |
| | 63 | 98.08 | 0.00 | 0.00 | 0.00 | 0.00 | 0.00 | 0.00 | 0.00 | 98.08 | 1.76 | 99.84 |
| | 90 | 98.05 | 0.00 | 0.00 | 0.00 | 0.00 | 0.00 | 0.00 | 0.00 | 98.05 | 1.82 | 99.87 |
| | Δ peak % in 90 d | 0.06 | 0.00 | 0.00 | 0.00 | 0.00 | 0.00 | 0.00 | 0.00 | | | |
| F8 | 0 | 97.98 | 0.00 | 0.00 | 0.00 | 0.00 | 0.00 | 0.00 | 0.00 | 97.98 | 1.90 | 99.88 |
| | 17 | 98.10 | 0.00 | 0.00 | 0.00 | 0.00 | 0.00 | 0.00 | 0.00 | 98.10 | 1.67 | 99.77 |
| | 38 | 98.25 | 0.00 | 0.00 | 0.00 | 0.00 | 0.00 | 0.00 | 0.00 | 98.25 | 1.75 | 100.00 |
| | 63 | 98.01 | 0.00 | 0.00 | 0.00 | 0.00 | 0.00 | 0.00 | 0.00 | 98.01 | 1.81 | 99.82 |
| | 90 | 98.03 | 0.00 | 0.00 | 0.00 | 0.00 | 0.00 | 0.00 | 0.00 | 98.03 | 1.84 | 99.87 |
| | Δ peak % in 90 d | 0.05 | 0.00 | 0.00 | 0.00 | 0.00 | 0.00 | 0.00 | 0.00 | | | |
| F9 | 0 | 97.93 | 0.00 | 0.00 | 0.00 | 0.00 | 0.00 | 0.00 | 0.00 | 97.93 | 1.94 | 99.87 |
| | 17 | 98.11 | 0.00 | 0.00 | 0.00 | 0.00 | 0.00 | 0.00 | 0.00 | 98.11 | 1.67 | 99.78 |
| | 38 | 98.20 | 0.00 | 0.00 | 0.00 | 0.00 | 0.00 | 0.00 | 0.00 | 98.20 | 1.64 | 99.84 |
| | 63 | 97.98 | 0.00 | 0.00 | 0.00 | 0.00 | 0.00 | 0.00 | 0.00 | 97.98 | 1.83 | 99.81 |
| | 90 | 97.83 | 0.00 | 0.00 | 0.00 | 0.00 | 0.00 | 0.00 | 0.00 | 97.83 | 2.05 | 99.88 |
| | Δ peak % in 90 d | −0.10 | 0.00 | 0.00 | 0.00 | 0.00 | 0.00 | 0.00 | 0.00 | | | |

Example 8—Stability Studies of Liquid Indacaterol and Glycopyrrolate Formulations A series of formulations of indacaterol in combination with glycopyrrolate were prepared for the stability study. Each formulation was initially prepared in a concentrated form and with a low pH to maximize the rate of indacaterol solubilization. Each formulation was transferred to a glass bottle, then indacaterol and glycopyrrolate was added. The formulation in the bottles were stirred by magnetic stirrer until the indacaterol had solubilized. The pH of each formulation was measured and subsequently adjusted with 2 N NaOH and/or 2 N HCl to the target pH. The stirring was allowed to stir for another 30 minutes. Water was added up to the target volume and the pH was checked to ensure target pH was maintained. Each formulation was filtered through a PVDF filter membrane to minimize particulate and microbial load and transferred to a biosafety cabinet (BSC) for vial filling. The osmolality and viscosity of the formulations were tested (see Table 14). Indacaterol and glycopyrrolate concentration and impurities were determined by RP-HPLC. RP-HPLC method parameters are outlined in Table 15.

The formulations were stored under various conditions and the appearance, pH, concentration, and impurities were tested at various time points to evaluate the stability of the formulations. For all formulations, except G1, appearance remained relatively unchanged over a 90-day period. For all formulations, the pH remained relatively unchanged over a 90-day period. For all formulations, the concentration of indacaterol and glycopyrrolate remained relatively unchanged over a 5-week period. Table 16, Table 17, and Table 18, show the appearance, pH, and drug concentration data for all formulations stored under various conditions. For all formulations, impurities at relative retention times of approximately 0.25, 0.29, 0.33, 0.60, 0.73, 0.83, 1.03, 1.10, and 1.15 remained relatively unchanged over a 5-week period. At the 40° C. storage condition only, minor increases in the quantity of the impurity at a relative retention time of 0.83 were observed for formulation G7, G8, and G9. A summary of the percentage change (90 d vs T0) in indacaterol main peak and total impurities is shown in Table 19, and full impurities data are shown in Table 20, Table 21, and Table 22.

TABLE 14

Liquid formulations of indacaterol and glycopyrrolate for stability studies.

| Name | Buffer (Citric Acid-Na Citrate) | pH | Excipients | Active Ingredient | Osmolality (mOsm/kg) | Viscosity (cP) |
|---|---|---|---|---|---|---|
| G1 | 50 mM | 3.0 | 290 mM mannitol | 200 µg/mL indacaterol base | 378.0 | 1.16 |
| G2 | | 4.0 | 10 mM NaCl | 200 µg/mL indacaterol base | 404.5 | 1.16 |
| G3 | 10 mM | 3.0 | 200 mM mannitol | 100 µg/mL indacaterol maleate | 239.5 | 1.10 |
| G4 | | 3.0 | | 50 µg/mL indacaterol maleate | 244.5 | 1.11 |
| G5 | | 4.0 | 10 mM NaCl | 100 µg/mL indacaterol maleate | 243.5 | 1.09 |
| G6 | | 4.0 | | 50 µg/mL indacaterol maleate | 240.5 | 1.17 |
| G7 | | 3.0 | | 500 µg/mL indacaterol base | 245.0 | 1.12 |
| G8 | | 3.0 | | 500 µg/mL indacaterol base 350 µg/mL glycopyrrolate bromide | 246.5 | 1.16 |
| G9 | | 3.5 | | 500 µg/mL indacaterol base 350 µg/mL glycopyrrolate bromide | 250.5 | 1.16 |

TABLE 15

RP-HPLC Concentration and Impurity Method Parameters (Examples 8-10)

| | |
|---|---|
| Column | Agilent InfinityLab Poroshell 120 Bonus-RP 2.7 µm, 4.6 × 100 mm |
| Reference Standard | Indacaterol Maleate |
| Mobile Phase A | 0.1% TFA in Water |
| Mobile Phase B | 0.1% TFA in ACN |
| Diluent | Methanol:Water:Acetic Acid (800:200:1) |
| Autosampler Temp. | 5° C. |
| Column Temp. | 40° C. |
| Injection Volume | 5 µL |
| Wavelength | 254 nm and 220 nm |
| Flow Rate | 1.5 mL/min |
| Run Time | 10 minutes |
| Elution Mode | Gradient |

| Time | % Mobile Phase A | % Mobile Phase B |
|---|---|---|
| 0 | 80.0 | 20.0 |
| 4 | 60.0 | 40.0 |
| 5 | 30.0 | 70.0 |
| 7 | 0.0 | 100.0 |
| 7.1 | 80.0 | 20.0 |
| 10 | 80.0 | 20.0 |

TABLE 16

Appearance, pH and concentration of indacaterol and glycopyrrolate liquid formulations stored at 40° C./75% RH for up to 5 weeks.

| Formulation | Timepoint (weeks) | Appearance | pH | Concentration (µg/mL) Indacaterol | Glycopyrrolate |
|---|---|---|---|---|---|
| G1 | 0 | Clear, colorless solution | 2.96 | 160.18 | n/a |
| | 1 | Clear, colorless solution | 2.86 | 164.32 | n/a |
| | 2 | Clear, colorless solution | 2.85 | 161.40 | n/a |

TABLE 16-continued

Appearance, pH and concentration of indacaterol and glycopyrrolate liquid formulations stored at 40° C./75% RH for up to 5 weeks.

| Formulation | Timepoint (weeks) | Appearance | pH | Concentration (μg/mL) Indacaterol | Glycopyrrolate |
|---|---|---|---|---|---|
| | 3 | Clear, colorless solution | 2.89 | 165.05 | n/a |
| | 4 | Clear, colorless solution | 2.88 | 165.78 | n/a |
| | 5 | Colorless solution with particulates | 2.84 | 170.14 | n/a |
| | Change in 5 weeks | n/a | −0.12 | +6.21* | n/a |
| G2 | 0 | Clear, colorless solution | 4.09 | 167.97 | n/a |
| | 1 | Clear, colorless solution | 3.90 | 156.00 | n/a |
| | 2 | Clear, colorless solution | 3.81 | 163.11 | n/a |
| | 3 | Clear, colorless solution | 3.89 | 160.28 | n/a |
| | 4 | Clear, colorless solution | 3.89 | 166.54 | n/a |
| | 5 | Colorless solution with particulates | 3.82 | 169.43 | n/a |
| | Change in 5 weeks | n/a | −0.27 | +0.86* | n/a |
| G3 | 0 | Clear, colorless solution | 3.01 | 70.58 | n/a |
| | 1 | Clear, colorless solution | 2.86 | 70.90 | n/a |
| | 2 | Clear, colorless solution | 2.82 | 70.85 | n/a |
| | 3 | Clear, colorless solution | 2.93 | 69.16 | n/a |
| | 4 | Clear, colorless solution | 2.89 | 69.86 | n/a |
| | 5 | Clear, colorless solution | 2.87 | 69.78 | n/a |
| | Change in 5 weeks | n/a | −0.14 | −1.14* | n/a |
| G4 | 0 | Clear, colorless solution | 3.04 | 31.10 | n/a |
| | 1 | Clear, colorless solution | 2.98 | 32.17 | n/a |
| | 2 | Clear, colorless solution | 2.93 | 32.03 | n/a |
| | 3 | Clear, colorless solution | 2.94 | 31.28 | n/a |
| | 4 | Clear, colorless solution | 2.96 | 30.95 | n/a |
| | 5 | Clear, colorless solution | 2.97 | 30.83 | n/a |
| | Change in 5 weeks | n/a | −0.07 | −0.88* | n/a |
| G5 | 0 | Clear, colorless solution | 4.00 | 70.90 | n/a |
| | 1 | Clear, colorless solution | 4.00 | 68.20 | n/a |
| | 2 | Clear, colorless solution | 3.99 | 69.36 | n/a |
| | 3 | Clear, colorless solution | 3.95 | 67.56 | n/a |
| | 4 | Clear, colorless solution | 3.98 | 68.36 | n/a |
| | 5 | Clear, colorless solution | 3.96 | 68.59 | n/a |
| | Change in 5 weeks | n/a | −0.04 | −3.25* | n/a |
| G6 | 0 | Clear, colorless solution | 4.02 | 32.01 | n/a |
| | 1 | Clear, colorless solution | 3.94 | 31.58 | n/a |
| | 2 | Clear, colorless solution | 3.90 | 31.74 | n/a |
| | 3 | Clear, colorless solution | 3.96 | 31.34 | n/a |
| | 4 | Clear, colorless solution | 3.96 | 31.96 | n/a |
| | 5 | Clear, colorless solution | 3.96 | 30.00 | n/a |
| | Change in 5 weeks | n/a | +0.02 | −6.29* | n/a |
| G7 | 0 | Clear, colorless solution | 3.03 | 447.08 | n/a |
| | 1 | Clear, colorless solution | 3.02 | 434.67 | n/a |
| | 2 | Clear, colorless solution | 2.89 | 466.13 | n/a |
| | 3 | Clear, colorless solution | 3.03 | 439.98 | n/a |
| | 4 | Clear, colorless solution | 2.94 | 448.97 | n/a |
| | 5 | Clear, colorless solution | 2.94 | 465.17 | n/a |
| | Change in 5 weeks | n/a | −0.09 | 4.05* | n/a |
| G8 | 0 | Clear, colorless solution | 3.04 | 448.24 | 320.50 |
| | 1 | Clear, colorless solution | 3.06 | 447.25 | 323.25 |
| | 2 | Clear, colorless solution | 3.06 | 454.01 | 327.65 |
| | 3 | Clear, colorless solution | 3.01 | 444.89 | n/a |
| | 4 | Clear, colorless solution | 3.05 | 438.77 | 326.71 |
| | 5 | Clear, colorless solution | 2.99 | TBD | TBD |
| | Change in 4 weeks | n/a | −0.05 | −2.11* | +1.94* |
| G9 | 0 | Clear, colorless solution | 3.46 | 443.55 | 328.18 |
| | 1 | Clear, colorless solution | 3.46 | 436.85 | 347.24 |
| | 2 | Clear, colorless solution | 3.35 | 445.01 | 327.28 |
| | 3 | Clear, colorless solution | 3.47 | 436.65 | 335.48 |
| | 4 | Clear, colorless solution | 3.48 | 436.49 | 338.85 |
| | 5 | Clear, colorless solution | 3.42 | TBD | TBD |
| | Change in 4 weeks | n/a | −0.04 | −1.59* | +3.25* |

*% change for value at final timepoint tested relative to Week 0.
TBD = To be determined.

TABLE 17

Appearance, pH and concentration of indacaterol and glycopyrrolate liquid formulations stored at 25° C./60% RH for 4 weeks.

| Formulation | Timepoint (weeks) | Appearance | pH | Concentration (μg/mL) Indacaterol | Glycopyrrolate |
|---|---|---|---|---|---|
| G1 | 0 | Clear, colorless solution | 2.96 | 160.18 | n/a |
|  | 1 | Clear, colorless solution | 2.91 | 140.74 | n/a |
|  | 2 | Colorless solution with particulates | 2.80 | 48.05 | n/a |
|  | 3 | Colorless solution with particulates | 2.89 | 36.59 | n/a |
|  | 4 | Colorless solution with particulates | 2.92 | 16.53 | n/a |
|  | Change in 4 weeks | n/a | −0.04 | −89.68* | n/a |
| G2 | 0 | Clear, colorless solution | 4.09 | 167.97 | n/a |
|  | 1 | Clear, colorless solution | 3.86 | 165.81 | n/a |
|  | 2 | Clear, colorless solution | 3.79 | 163.52 | n/a |
|  | 3 | Clear, colorless solution | 3.85 | 160.65 | n/a |
|  | 4 | Clear, colorless solution | 3.91 | 170.70 | n/a |
|  | Change in 4 weeks | n/a | −0.18 | +1.62* | n/a |
| G3 | 0 | Clear, colorless solution | 3.01 | 70.58 | n/a |
|  | 1 | Clear, colorless solution | 2.94 | 70.51 | n/a |
|  | 2 | Colorless solution one particulate | 2.80 | 69.95 | n/a |
|  | 3 | Clear, colorless solution | 2.88 | 69.10 | n/a |
|  | 4 | Clear, colorless solution | 2.93 | 68.85 | n/a |
|  | Change in 4 weeks | n/a | 0.08 | −2.46* | n/a |
| G4 | 0 | Clear, colorless solution | 3.04 | 31.10 | n/a |
|  | 1 | Clear, colorless solution | 2.93 | 31.26 | n/a |
|  | 2 | Clear, colorless solution | 2.91 | 31.48 | n/a |
|  | 3 | Clear, colorless solution | 3.03 | 31.86 | n/a |
|  | 4 | Clear, colorless solution | 2.97 | 31.70 | n/a |
|  | Change in 4 weeks | n/a | −0.07 | +1.94* | n/a |
| G5 | 0 | Clear, colorless solution | 4.00 | 70.90 | n/a |
|  | 1 | Colorless solution with particulates | 3.98 | 68.33 | n/a |
|  | 2 | Colorless solution with particulates | 3.97 | 67.98 | n/a |
|  | 3 | Colorless solution with particulates | 3.97 | 68.62 | n/a |
|  | 4 | Colorless solution with particulates | 3.99 | 68.68 | n/a |
|  | Change in 4 weeks | n/a | −0.01 | −3.13* | n/a |
| G6 | 0 | Clear, colorless solution | 4.02 | 32.01 | n/a |
|  | 1 | Clear, colorless solutions | 4.02 | 31.37 | n/a |
|  | 2 | Clear, colorless solution | 3.92 | 31.91 | n/a |
|  | 3 | Clear, colorless solution | 3.99 | 31.48 | n/a |
|  | 4 | Clear, colorless solutions | 4.01 | 31.69 | n/a |
|  | Change in 4 weeks | n/a | −0.01 | −1.00* | n/a |
| G7 | 0 | Clear, colorless solution | 3.03 | 447.08 | n/a |
|  | 1 | Clear, colorless solution | 2.99 | 446.94 | n/a |
|  | 2 | Clear, colorless solution | 2.90 | 445.44 | n/a |
|  | 3 | Clear, colorless solution | 3.02 | 433.43 | n/a |
|  | 4 | Clear, colorless solution | 3.02 | 448.07 | n/a |
|  | Change in 4 weeks | n/a | −0.01 | +0.22* | n/a |
| G8 | 0 | Clear, colorless solution | 3.04 | 448.24 | 320.50 |
|  | 1 | Clear, colorless solution | 3.01 | 453.50 | 345.51 |
|  | 2 | Clear, colorless solution | 2.98 | 451.48 | 329.12 |
|  | 3 | Clear, colorless solution | 3.07 | 442.78 | 352.68 |
|  | 4 | Clear, colorless solution | 3.04 | 436.96 | 312.27 |
|  | Change in 4 weeks | n/a | 0.00 | −2.52* | −2.57* |
| G9 | 0 | Clear, colorless solution | 3.46 | 443.55 | 328.18 |
|  | 1 | Clear, colorless solution | 3.43 | 436.92 | 312.31 |
|  | 2 | Clear, colorless solution | 3.41 | 440.29 | 312.58 |
|  | 3 | Clear, colorless solution | 3.48 | 437.07 | 356.05 |
|  | 4 | Clear, colorless solution | 3.43 | 440.89 | 359.28 |
|  | Change in 4 weeks | n/a | +0.03 | −0.60* | +9.48* |

*% change for value at final timepoint tested relative to Week 0.

TABLE 18

Appearance, pH and concentration of indacaterol and glycopyrrolate liquid formulations stored at 5° C. for 4 weeks.

| Formulation | Timepoint (weeks) | Appearance | pH | Concentration (μg/mL) Indacaterol | Glycopyrrolate |
|---|---|---|---|---|---|
| G1 | 0 | Clear, colorless solution | 2.96 | 160.18 | n/a |
|  | 1 | Colorless solution with particulates | 2.89 | 15.88 | n/a |
|  | 2 | Colorless solution with particulates | 2.73 | 5.11 | n/a |

TABLE 18-continued

Appearance, pH and concentration of indacaterol and glycopyrrolate liquid formulations stored at 5° C. for 4 weeks.

| Formulation | Timepoint (weeks) | Appearance | pH | Concentration (μg/mL) Indacaterol | Glycopyrrolate |
|---|---|---|---|---|---|
| | 3 | Colorless solution with particulates | 2.88 | 2.74 | n/a |
| | 4 | Colorless solution with particulates | 2.90 | 3.57 | n/a |
| | Change in 4 weeks | n/a | −0.06 | −97.77* | n/a |
| G2 | 0 | Clear, colorless solution | 4.09 | 167.97 | n/a |
| | 1 | Clear, colorless solution | 3.91 | 165.81 | n/a |
| | 2 | Clear, colorless solution | 3.89 | 164.76 | n/a |
| | 3 | Clear, colorless solution | 3.88 | 161.84 | n/a |
| | 4 | Clear, colorless solution | 3.90 | 168.04 | n/a |
| | Change in 4 weeks | n/a | −0.19 | +0.04* | n/a |
| G3 | 0 | Clear, colorless solution | 3.01 | 70.58 | n/a |
| | 1 | Clear, colorless solution | 2.93 | 70.99 | n/a |
| | 2 | Clear, colorless solution | 2.77 | 69.73 | n/a |
| | 3 | Clear, colorless solution | 2.91 | 71.84 | n/a |
| | 4 | Clear, colorless solution | 2.97 | 69.61 | n/a |
| | Change in 4 weeks | n/a | −0.04 | −1.38* | n/a |
| G4 | 0 | Clear, colorless solution | 3.04 | 31.10 | n/a |
| | 1 | Clear, colorless solution | 2.96 | 32.17 | n/a |
| | 2 | Clear, colorless solution | 2.91 | 31.74 | n/a |
| | 3 | Clear, colorless solution | 3.04 | 31.86 | n/a |
| | 4 | Clear, colorless solution | 3.05 | 31.39 | n/a |
| | Change in 4 weeks | n/a | +0.01 | +0.93* | n/a |
| G5 | 0 | Clear, colorless solution | 4.00 | 70.90 | n/a |
| | 1 | Clear, colorless solution | 3.97 | 69.03 | n/a |
| | 2 | Clear, colorless solution | 3.92 | 68.67 | n/a |
| | 3 | Clear, colorless solution | 3.94 | 69.10 | n/a |
| | 4 | Clear, colorless solution | 4.04 | 68.87 | n/a |
| | Change in 4 weeks | n/a | +0.04 | −2.85* | n/a |
| G6 | 0 | Clear, colorless solution | 4.02 | 32.01 | n/a |
| | 1 | Clear, colorless solution | 3.95 | 31.98 | n/a |
| | 2 | Clear, colorless solution | 3.98 | 31.89 | n/a |
| | 3 | Clear, colorless solution | 3.97 | 32.23 | n/a |
| | 4 | Clear, colorless solution | 4.02 | 31.80 | n/a |
| | Change in 4 weeks | n/a | 0.00 | −0.67* | n/a |
| G7 | 0 | Clear, colorless solution | 3.03 | 447.08 | n/a |
| | 1 | Clear, colorless solution | 2.98 | 434.67 | n/a |
| | 2 | Clear, colorless solution | 2.92 | 445.44 | n/a |
| | 3 | Clear, colorless solution | 3.01 | 438.41 | n/a |
| | 4 | Clear, colorless solution | 3.04 | 451.58 | n/a |
| | Change in 4 weeks | n/a | +0.01 | +1.01* | n/a |
| G8 | 0 | Clear, colorless solution | 3.04 | 448.24 | 320.50 |
| | 1 | Clear, colorless solution | 3.05 | 440.68 | 320.62 |
| | 2 | Clear, colorless solution | 3.02 | 451.48 | 328.66 |
| | 3 | Clear, colorless solution | 3.11 | 421.05 | 298.22 |
| | 4 | Clear, colorless solution | 3.07 | 431.34 | 321.22 |
| | Change in 4 weeks | n/a | +0.03 | −3.77* | +0.22* |
| G9 | 0 | Clear, colorless solution | 3.46 | 443.55 | 328.18 |
| | 1 | Clear, colorless solution | 3.43 | 439.71 | 336.65 |
| | 2 | Clear, colorless solution | 3.44 | 440.29 | 345.13 |
| | 3 | Clear, colorless solution | 3.43 | 453.03 | 343.91 |
| | 4 | Clear, colorless solution | 3.47 | 437.87 | 353.16 |
| | Change in 4 weeks | n/a | +0.01 | −1.28* | +7.61* |

*% change for value at final timepoint tested relative to Week 0.

TABLE 19

Summary of % change (4 weeks or 5 weeks vs T0) in indacaterol main peak and total product-related impurities for indacaterol liquid formulations stored at various conditions. Detection at 254 nm.

| Formulation | | | | % Change of Indacaterol Purity (vs Time 0) | | | | | |
|---|---|---|---|---|---|---|---|---|---|
| | Buffer | | | 40° C./75% RH[1] | | 25° C./60% RH[2] | | 5° C.[2] | |
| Name | (Citric Acid-Na Citrate) | Excipients | pH | Indacaterol Main Peak | Impurities | Indacaterol Main Peak | Impurities | Indacaterol Main Peak | Impurities |
| G2 | 50 mM | 290 mM mannitol | 3.0 | −2.065 | 1.782 | −0.500 | −0.043 | −0.042 | 0.048 |
| G3 | | 10 mM NaCl | 4.0 | −0.911 | 0.956 | 0.043 | 0.011 | −0.284 | 0.329 |
| G4 | 10 mM | 200 mM mannitol | 3.0 | −1.522 | 1.522 | 0.034 | −0.144 | −0.482 | 0.482 |
| G5 | | 10 mM NaCl | 3.0 | −1.186 | 1.107 | 0.144 | −0.151 | −0.183 | 0.184 |
| G6 | | | 4.0 | −1.476 | 1.387 | 0.15 | −0.459 | −0.086 | 0.086 |
| G7 | | | 4.0 | −0.444 | 0.415 | 0.46 | −0.015 | 0.000 | 0.021 |
| G8 | | | 3.0 | −0.432 | 0.403 | −0.005 | −0.031 | −0.001 | −0.003 |
| G9 | | | 3.5 | −0.623 | 0.538 | 0.013 | −0.012 | −0.028 | 0.022 |

[1]% change at 5 weeks vs Time 0
[2]% change at 4 weeks vs Time 0

TABLE 20

% main peak and % impurities for indacaterol liquid formulations stored at 40° C./75% RH for 5 weeks. Detection at 254 nm.

| Formulation | Timepoint (weeks) | Indacaterol (%) | Impurities (product and process-related) (%) | | | | | | | | | Total Impurities | Total area |
|---|---|---|---|---|---|---|---|---|---|---|---|---|---|
| | | | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | | |
| F1 | 0 | 98.318 | 0.3 | 0 | 0.032 | 0.053 | 0 | 0.004 | 0 | 1.163 | 0.116 | 1.668 | 100.002 |
| | 1 | 97.957 | 0.454 | 0 | 0.018 | 0.084 | 0 | 0.127 | 0 | 1.202 | 0.13 | 2.015 | 99.986 |
| | 2 | 97.766 | 0.643 | 0 | 0 | 0.064 | 0 | 0.167 | 0 | 1.202 | 0.124 | 2.2 | 99.972 |
| | 3 | 98.242 | 0.108 | 0 | 0.036 | 0.056 | 0 | 0.184 | 0 | 1.213 | 0.119 | 1.716 | 99.966 |
| | 4 | 97.054 | 1.086 | 0.255 | 0.038 | 0.068 | 0 | 0.24 | 0 | 1.088 | 0.128 | 2.903 | 99.958 |
| | 5 | 98.318 | 0.3 | 0 | 0.032 | 0.053 | 0 | 0.004 | 0 | 1.163 | 0.116 | 1.668 | 99.957 |
| | % change in 5 weeks | −1.291 | 0.879 | 0.217 | 0.014 | 0.012 | 0 | 0.24 | 0 | −0.125 | 0.009 | 2.903 | −0.045 |
| F2 | 0 | 98.386 | 0.192 | 0.03 | 0 | 0.067 | 0 | 0 | 0 | 1.199 | 0.121 | 1.609 | 99.995 |
| | 1 | 98.107 | 0.296 | 0.254 | 0 | 0 | 0 | 0 | 0 | 1.203 | 0.128 | 1.881 | 99.988 |
| | 2 | 97.569 | 0.415 | 0.427 | 0.012 | 0.088 | 0 | 0.128 | 0 | 1.198 | 0.112 | 2.38 | 99.949 |
| | 3 | 97.078 | 0.618 | 0.539 | 0.049 | 0.052 | 0 | 0.187 | 0 | 1.202 | 0.113 | 2.76 | 99.838 |
| | 4 | 97.275 | 0.212 | 0.63 | 0.059 | 0.052 | 0 | 0.195 | 0 | 1.203 | 0.138 | 2.489 | 99.764 |
| | 5 | 96.321 | 0.971 | 0.678 | 0.085 | 0.053 | 0 | 0.285 | 0 | 1.183 | 0.136 | 3.391 | 99.712 |
| | % change in 5 weeks | −2.065 | 0.779 | 0.648 | 0.085 | −0.014 | 0 | 0.285 | 0 | −0.016 | 0.015 | 1.782 | −0.283 |
| F3 | 0 | 97.329 | 2.378 | 0 | 0 | 0 | 0 | 0 | 0.248 | 0 | 0 | 2.626 | 99.955 |
| | 1 | 96.573 | 3.014 | 0 | 0.046 | 0.097 | 0 | 0 | 0.226 | 0.045 | 0 | 3.428 | 100.001 |
| | 2 | 96.753 | 2.809 | 0 | 0.036 | 0.084 | 0.034 | 0 | 0.246 | 0.038 | 0 | 3.247 | 100 |
| | 3 | 97.013 | 2.58 | 0 | 0.033 | 0.083 | 0.025 | 0 | 0.23 | 0.035 | 0 | 2.986 | 99.999 |
| | 4 | 97.161 | 2.305 | 0 | | 0.108 | 0.033 | 0.111 | 0.25 | 0.032 | 0 | 2.839 | 100 |
| | 5 | 96.418 | 3.049 | 0 | 0.024 | 0.094 | 0 | 0.124 | 0.249 | 0.042 | 0 | 3.582 | 100 |
| | % change in 5 weeks | −0.911 | 0.671 | 0 | 0.024 | 0.094 | 0 | 0.124 | 0.001 | 0.042 | 0 | 0.956 | 0.045 |
| F4 | 0 | 96.917 | 2.808 | 0 | 0.027 | 0 | 0 | 0 | 0.248 | 0 | 0 | 3.083 | 100 |
| | 1 | 95.562 | 4.083 | 0 | 0 | 0.084 | 0 | 0 | 0.27 | 0 | 0 | 4.437 | 99.999 |
| | 2 | 95.883 | 3.714 | 0 | 0.069 | 0.087 | 0 | 0 | 0.248 | 0 | 0 | 4.118 | 100.001 |
| | 3 | 96.554 | 3.141 | 0 | 0.069 | 0 | 0 | 0 | 0.236 | 0 | 0 | 3.446 | 100 |
| | 4 | 97.028 | 2.655 | 0 | 0 | 0.097 | 0 | 0 | 0.22 | 0 | 0 | 2.972 | 100 |
| | 5 | 95.395 | 4.185 | 0 | 0 | 0.101 | 0 | 0.113 | 0.206 | 0 | 0 | 4.605 | 100 |
| | % change in 5 weeks | −1.522 | 1.377 | 0 | −0.027 | 0.101 | 0 | 0.113 | −0.042 | 0 | 0 | 1.522 | 0 |
| F5 | 0 | 97.189 | 2.546 | 0 | 0 | 0 | 0 | 0 | 0.265 | 0 | 0 | 2.811 | 100 |
| | 1 | 96.573 | 3.074 | 0 | 0 | 0.088 | 0.028 | 0 | 0.238 | 0 | 0 | 3.428 | 100.001 |
| | 2 | 96.735 | 2.839 | 0 | 0.034 | 0.09 | 0.024 | 0 | 0.244 | 0.033 | 0 | 3.264 | 99.999 |
| | 3 | 96.77 | 2.565 | 0.202 | 0.029 | 0.107 | 0 | 0 | 0.247 | 0.043 | 0 | 3.193 | 99.963 |
| | 4 | 97.138 | 2.338 | 0 | 0 | 0.079 | 0.031 | 0.103 | 0.247 | 0 | 0 | 2.798 | 99.936 |
| | 5 | 96.003 | 3.09 | 0.312 | 0 | 0.09 | 0.03 | 0.127 | 0.209 | 0.06 | 0 | 3.918 | 99.921 |
| | % change in 5 weeks | −1.186 | 0.544 | 0.312 | 0 | 0.09 | 0.03 | 0.127 | −0.056 | 0.06 | 0 | 1.107 | −0.079 |
| F6 | 0 | 96.705 | 2.989 | 0 | 0 | 0 | 0 | 0 | 0.306 | 0 | 0 | 3.295 | 100 |
| | 1 | 95.481 | 4.144 | 0 | 0 | 0.099 | 0 | 0 | 0.25 | 0.026 | 0 | 4.519 | 100 |
| | 2 | 95.87 | 3.686 | 0 | 0.081 | 0.13 | 0 | 0 | 0.232 | 0 | 0 | 4.129 | 99.999 |
| | 3 | 96.597 | 3.074 | 0 | 0.07 | 0 | 0 | 0 | 0.258 | 0 | 0 | 3.402 | 99.999 |

TABLE 20-continued

% main peak and % impurities for indacaterol liquid formulations stored at 40° C./75% RH for 5 weeks. Detection at 254 nm.

| Formulation | Timepoint (weeks) | Indacaterol (%) | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | Total Impurities | Total area |
|---|---|---|---|---|---|---|---|---|---|---|---|---|---|
| | 4 | 97.017 | 2.56 | 0 | 0 | 0.107 | 0 | 0 | 0.248 | 0 | 0 | 2.915 | 99.932 |
| | 5 | 95.229 | 4.267 | 0 | 0.045 | 0.123 | 0 | 0 | 0.217 | 0.03 | 0 | 4.682 | 99.911 |
| | % change in 5 weeks | −1.476 | 1.278 | 0 | 0.045 | 0.123 | 0 | 0 | −0.089 | 0.03 | 0 | 1.387 | −0.089 |
| F7 | 0 | 98.477 | 0.095 | 0 | 0 | 0.052 | 0 | 0 | 0 | 1.216 | 0.121 | 1.484 | 99.961 |
| | 1 | 98.39 | 0.141 | 0 | 0.004 | 0.051 | 0 | 0 | 0 | 1.216 | 0.12 | 1.532 | 99.922 |
| | 2 | 98.343 | 0.17 | 0 | 0 | 0.054 | 0 | 0.041 | 0 | 1.214 | 0.12 | 1.599 | 99.942 |
| | 3 | 98.181 | 0.301 | 0 | 0 | 0.063 | 0 | 0.103 | 0 | 1.214 | 0.114 | 1.795 | 99.976 |
| | 4 | 98.367 | 0.079 | 0 | 0.011 | 0.048 | 0 | 0.114 | 0 | 1.198 | 0.117 | 1.567 | 99.934 |
| | 5 | 98.033 | 0.396 | 0 | 0.007 | 0.055 | 0 | 0.135 | 0 | 1.192 | 0.114 | 1.899 | 99.932 |
| | % change in 5 weeks | −0.444 | 0.301 | 0 | 0.007 | 0.003 | 0 | 0.135 | 0 | −0.024 | −0.007 | 0.415 | −0.029 |
| F8 | 0 | 97.766 | 0.102 | 0 | 0.001 | 0.059 | 0.705 | 0 | 0 | 1.21 | 0.12 | 2.197 | 99.963 |
| | 1 | 97.714 | 0.129 | 0 | 0 | 0.055 | 0.705 | 0 | 0 | 1.207 | 0.121 | 2.217 | 99.931 |
| | 2 | 97.617 | 0.198 | 0 | 0 | 0.057 | 0.702 | 0.078 | 0 | 1.187 | 0.123 | 2.345 | 99.962 |
| | 3 | 98.159 | 0.303 | 0 | 0.007 | 0.055 | 0 | 0.108 | 0 | 1.194 | 0.12 | 1.787 | 99.946 |
| | 4 | 97.665 | 0.079 | 0 | 0.012 | 0.049 | 0.706 | 0.132 | 0 | 1.193 | 0.117 | 2.288 | 99.953 |
| | 5 | 97.334 | 0.39 | 0 | 0.008 | 0.053 | 0.697 | 0.145 | 0 | 1.191 | 0.116 | 2.6 | 99.934 |
| | % change in 5 weeks | −0.432 | 0.288 | 0 | 0.007 | −0.006 | −0.008 | 0.145 | 0 | −0.019 | −0.004 | 0.403 | −0.029 |
| F9 | 0 | 97.777 | 0.109 | 0 | 0 | 0.05 | 0.71 | 0 | 0 | 1.202 | 0.118 | 2.189 | 99.966 |
| | 1 | 97.729 | 0.153 | 0 | 0.002 | 0.052 | 0.726 | 0 | 0 | 1.2 | 0.119 | 2.252 | 99.981 |
| | 2 | 97.591 | 0.216 | 0 | 0.008 | 0.046 | 0.725 | 0.061 | 0 | 1.201 | 0.115 | 2.372 | 99.963 |
| | 3 | 97.361 | 0.32 | 0.075 | 0.004 | 0.057 | 0.719 | 0.101 | 0 | 1.198 | 0.119 | 2.593 | 99.954 |
| | 4 | 97.54 | 0.086 | 0.085 | 0.011 | 0.054 | 0.719 | 0.126 | 0 | 1.175 | 0.115 | 2.371 | 99.911 |
| | 5 | 97.154 | 0.399 | 0.13 | 0.012 | 0.054 | 0.7 | 0.132 | 0 | 1.178 | 0.122 | 2.727 | 99.881 |
| | % change in 5 weeks | −0.623 | 0.29 | 0.13 | 0.012 | 0.004 | −0.01 | 0.132 | 0 | −0.024 | 0.004 | 0.538 | −0.085 |

TABLE 21

% main peak and % impurities for indacaterol liquid formulations stored at 25° C./60% RH for 5 weeks. Detection at 254 nm.

| Formulation | Timepoint (weeks) | Indacaterol (%) | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | Total Impurities | Total area |
|---|---|---|---|---|---|---|---|---|---|---|---|---|---|
| F1 | 0 | 98.345 | 0.207 | 0.038 | 0.024 | 0.056 | 0 | 0 | 0 | 1.213 | 0.119 | 1.668 | 100.002 |
| | 1 | 97.714 | 0.824 | 0.037 | 0.102 | 0.074 | 0 | 0 | 0 | 1.116 | 0.133 | 2.286 | 100 |
| | 2 | 95.99 | 2.976 | 0.049 | 0.214 | 0 | 0 | 0 | 0 | 0.56 | 0.21 | 4.009 | 99.999 |
| | 3 | 95.484 | 3.51 | 0.035 | 0.25 | 0 | 0 | 0 | 0 | 0.504 | 0.208 | 4.507 | 99.991 |
| | 4 | 97.845 | 1.304 | 0 | 0.422 | 0 | 0 | 0 | 0 | 0 | 0.429 | 2.155 | 100 |
| | % change in 4 weeks | −0.5 | 1.097 | −0.038 | 0.398 | −0.056 | 0 | 0 | 0 | −1.213 | 0.31 | 0.498 | −0.002 |
| F2 | 0 | 98.386 | 0.192 | 0.03 | 0 | 0.067 | 0 | 0 | 0 | 1.199 | 0.121 | 1.609 | 99.995 |
| | 1 | 97.667 | 0.87 | 0.02 | 0.072 | 0.057 | 0 | 0 | 0 | 1.189 | 0.125 | 2.333 | 100 |
| | 2 | 97.448 | 1.128 | 0 | 0.102 | 0.055 | 0 | 0 | 0 | 1.131 | 0.13 | 2.546 | 99.994 |
| | 3 | 97.459 | 1.09 | 0.025 | 0.085 | 0.061 | 0 | 0 | 0 | 1.126 | 0.139 | 2.526 | 99.985 |
| | 4 | 98.429 | 0.19 | 0 | 0.066 | 0.043 | 0 | 0 | 0 | 1.146 | 0.121 | 1.566 | 99.995 |
| | % change in 4 weeks | 0.043 | −0.002 | −0.03 | 0.066 | −0.024 | 0 | 0 | 0 | −0.053 | 0 | −0.043 | 0 |
| F3 | 0 | 97.329 | 2.378 | 0 | 0 | 0 | 0 | 0 | 0.248 | 0 | 0 | 2.626 | 99.955 |
| | 1 | 96.629 | 2.942 | 0 | 0.047 | 0.074 | 0.029 | 0 | 0.245 | 0.034 | 0 | 3.371 | 100 |
| | 2 | 96.803 | 2.767 | 0 | 0.04 | 0.104 | 0 | 0 | 0.245 | 0.04 | 0 | 3.196 | 99.999 |
| | 3 | 97.204 | 2.432 | 0 | 0 | 0.083 | 0 | 0 | 0.242 | 0.038 | 0 | 2.795 | 99.999 |
| | 4 | 97.363 | 2.253 | 0 | 0 | 0.084 | 0 | 0 | 0.253 | 0.047 | 0 | 2.637 | 100 |
| | % change in 4 weeks | 0.034 | −0.125 | 0 | 0 | 0.084 | 0 | 0 | 0.005 | 0.047 | 0 | 0.011 | 0.045 |
| F4 | 0 | 96.917 | 2.808 | 0 | 0.027 | 0 | 0 | 0 | 0.248 | 0 | 0 | 3.083 | 100 |
| | 1 | 95.517 | 4.076 | 0 | 0.08 | 0.075 | 0 | 0 | 0.252 | 0 | 0 | 4.483 | 100 |
| | 2 | 96.069 | 3.534 | 0 | 0.078 | 0.099 | 0 | 0 | 0.219 | 0 | 0 | 3.93 | 99.999 |
| | 3 | 96.799 | 2.87 | 0 | 0 | 0.104 | 0 | 0 | 0.227 | 0 | 0 | 3.201 | 100 |
| | 4 | 97.061 | 2.512 | 0 | 0.088 | 0.111 | 0 | 0 | 0.228 | 0 | 0 | 2.939 | 100 |
| | % change in 4 weeks | 0.144 | −0.296 | 0 | 0.061 | 0.111 | 0 | 0 | −0.02 | 0 | 0 | −0.144 | 0 |
| F5 | 0 | 97.189 | 2.546 | 0 | 0 | 0 | 0 | 0 | 0.265 | 0 | 0 | 2.811 | 100 |
| | 1 | 96.56 | 3.044 | 0 | 0.041 | 0.106 | 0 | 0 | 0.248 | 0 | 0 | 3.439 | 99.999 |

TABLE 21-continued

% main peak and % impurities for indacaterol liquid formulations stored at 25° C./60% RH for 5 weeks. Detection at 254 nm.

| Formulation | Timepoint (weeks) | Indacaterol (%) | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | Total Impurities | Total area |
|---|---|---|---|---|---|---|---|---|---|---|---|---|---|
| | 2 | 96.811 | 2.757 | 0 | 0.044 | 0.114 | 0.033 | 0 | 0.241 | 0 | 0 | 3.189 | 100 |
| | 3 | 97.169 | 2.451 | 0 | 0 | 0.091 | 0.019 | 0 | 0.271 | 0 | 0 | 2.832 | 100.001 |
| | 4 | 97.339 | 2.285 | 0 | 0 | 0.099 | 0.028 | 0 | 0.248 | 0 | 0 | 2.66 | 99.999 |
| | % change in 4 weeks | 0.15 | −0.261 | 0 | 0 | 0.099 | 0.028 | 0 | −0.017 | 0 | 0 | −0.151 | −0.001 |
| F6 | 0 | 96.705 | 2.989 | 0 | 0 | 0 | 0 | 0 | 0.306 | 0 | 0 | 3.295 | 100 |
| | 1 | 95.468 | 4.074 | 0 | 0.074 | 0.142 | 0 | 0 | 0.242 | 0 | 0 | 4.532 | 100 |
| | 2 | 96.071 | 3.463 | 0 | 0.091 | 0.156 | 0 | 0 | 0.22 | 0 | 0 | 3.93 | 100.001 |
| | 3 | 96.765 | 2.832 | 0 | 0 | 0.157 | 0 | 0 | 0.246 | 0 | 0 | 3.235 | 100 |
| | 4 | 97.165 | 2.486 | 0 | 0 | 0.108 | 0 | 0 | 0.242 | 0 | 0 | 2.836 | 100.001 |
| | % change in 4 weeks | 0.46 | −0.503 | 0 | 0 | 0.108 | 0 | 0 | −0.064 | 0 | 0 | −0.459 | 0.001 |
| F7 | 0 | 98.477 | 0.095 | 0 | 0 | 0.052 | 0 | 0 | 0 | 1.216 | 0.121 | 1.484 | 99.961 |
| | 1 | 98.164 | 0.398 | 0 | 0.009 | 0.061 | 0 | 0 | 0 | 1.191 | 0.12 | 1.779 | 99.943 |
| | 2 | 98.097 | 0.465 | 0 | 0 | 0.067 | 0 | 0 | 0 | 1.191 | 0.125 | 1.848 | 99.945 |
| | 3 | 98.129 | 0.432 | 0 | 0 | 0.056 | 0 | 0 | 0 | 1.191 | 0.125 | 1.804 | 99.933 |
| | 4 | 98.472 | 0.093 | 0 | 0.002 | 0.047 | 0 | 0 | 0 | 1.2 | 0.127 | 1.469 | 99.941 |
| | % change in 4 weeks | −0.005 | −0.002 | 0 | 0.002 | −0.005 | 0 | 0 | 0 | −0.016 | 0.006 | −0.015 | −0.02 |
| F8 | 0 | 97.766 | 0.102 | 0 | 0.001 | 0.059 | 0.705 | 0 | 0 | 1.21 | 0.12 | 2.197 | 99.963 |
| | 1 | 97.482 | 0.391 | 0 | 0.006 | 0.053 | 0.706 | 0 | 0 | 1.181 | 0.123 | 2.46 | 99.942 |
| | 2 | 97.435 | 0.44 | 0 | 0.002 | 0.057 | 0.707 | 0 | 0 | 1.185 | 0.122 | 2.513 | 99.948 |
| | 3 | 97.438 | 0.43 | 0 | 0 | 0.05 | 0.711 | 0 | 0 | 1.184 | 0.121 | 2.496 | 99.934 |
| | 4 | 97.779 | 0.094 | 0 | 0.003 | 0.048 | 0.708 | 0 | 0 | 1.192 | 0.121 | 2.166 | 99.945 |
| | % change in 4 weeks | 0.013 | −0.008 | 0 | 0.002 | −0.011 | 0.003 | 0 | 0 | −0.018 | 0.001 | −0.031 | −0.018 |
| F9 | 0 | 97.777 | 0.109 | 0 | 0 | 0.05 | 0.71 | 0 | 0 | 1.202 | 0.118 | 2.189 | 99.966 |
| | 1 | 97.447 | 0.425 | 0 | 0 | 0.06 | 0.715 | 0 | 0 | 1.199 | 0.118 | 2.517 | 99.964 |
| | 2 | 97.422 | 0.461 | 0.001 | 0.006 | 0.048 | 0.708 | 0 | 0 | 1.178 | 0.122 | 2.524 | 99.946 |
| | 3 | 97.417 | 0.443 | 0.007 | 0.006 | 0.05 | 0.718 | 0 | 0 | 1.176 | 0.122 | 2.522 | 99.939 |
| | 4 | 97.747 | 0.095 | 0 | 0 | 0.051 | 0.726 | 0 | 0 | 1.185 | 0.12 | 2.177 | 99.924 |
| | % change in 4 weeks | −0.03 | −0.014 | 0 | 0 | 0.001 | 0.016 | 0 | 0 | −0.017 | 0.002 | −0.012 | −0.042 |

TABLE 22

% main peak and % impurities for indacaterol liquid formulations stored at 5° C. for 5 weeks. Detection at 254 nm.

| Formulation | Timepoint (weeks) | Indacaterol (%) | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | Total Impurities | Total area |
|---|---|---|---|---|---|---|---|---|---|---|---|---|---|
| F1 | 0 | 98.318 | 0.3 | 0 | 0.032 | 0.053 | 0 | 0.004 | 0 | 1.163 | 0.116 | 1.668 | 100.002 |
| | 1 | 97.458 | 1.097 | 0.036 | 0.094 | 0.067 | 0 | 0 | 0 | 1.12 | 0.128 | 2.542 | 100 |
| | 2 | 95.954 | 2.763 | 0.05 | 0.19 | 0 | 0 | 0 | 0 | 0.88 | 0.153 | 4.036 | 99.99 |
| | 3 | 94.75 | 3.826 | 0.167 | 0.296 | 0 | 0 | 0 | 0 | 0.793 | 0.167 | 5.249 | 99.999 |
| | 4 | 95.377 | 2.867 | 0.355 | 0.812 | 0 | 0 | 0 | 0 | 0.526 | | 4.56 | 99.937 |
| | % change in 4 weeks | −2.968 | 2.66 | 0.317 | 0.788 | −0.056 | 0 | 0 | 0 | −0.687 | −0.119 | 2.903 | −0.065 |
| F2 | 0 | 98.386 | 0.192 | 0.03 | 0 | 0.067 | 0 | 0 | 0 | 1.199 | 0.121 | 1.609 | 99.995 |
| | 1 | 97.498 | 1.077 | 0.018 | 0.086 | 0.063 | 0 | 0 | 0 | 1.132 | 0.126 | 2.502 | 100 |
| | 2 | 97.488 | 1.1 | 0.011 | 0.086 | 0.054 | 0 | 0 | 0 | 1.128 | 0.132 | 2.511 | 99.999 |
| | 3 | 97.6 | 0.969 | 0.026 | 0.089 | 0.051 | 0 | 0 | 0 | 1.137 | 0.128 | 2.4 | 100 |
| | 4 | 98.344 | 0.226 | 0.03 | 0.1 | 0.041 | 0 | 0 | 0 | 1.132 | 0.128 | 1.657 | 100.001 |
| | % change in 4 weeks | −0.042 | 0.034 | 0 | 0.1 | −0.026 | 0 | 0 | 0 | −0.067 | 0.007 | 0.048 | 0.006 |
| F3 | 0 | 97.329 | 2.378 | 0 | 0 | 0 | 0 | 0 | 0.248 | 0 | 0 | 2.626 | 99.955 |
| | 1 | 96.652 | 2.946 | 0 | 0 | 0.086 | 0.026 | 0 | 0.24 | 0 | 0 | 3.298 | 99.95 |
| | 2 | 96.979 | 2.556 | 0 | 0.035 | 0.076 | 0.034 | 0 | 0.227 | 0.048 | 0 | 2.976 | 99.955 |
| | 3 | 97.185 | 2.389 | 0 | 0 | 0.102 | 0.029 | 0 | 0.26 | 0 | 0 | 2.78 | 99.965 |
| | 4 | 97.045 | 2.568 | 0 | 0 | 0.098 | 0.024 | 0 | 0.265 | 0 | 0 | 2.955 | 100 |
| | % change in 4 weeks | −0.284 | 0.19 | 0 | 0 | 0.098 | 0.024 | 0 | 0.017 | 0 | 0 | 0.329 | 0.045 |
| F4 | 0 | 96.917 | 2.808 | 0 | 0.027 | 0 | 0 | 0 | 0.248 | 0 | 0 | 3.083 | 100 |
| | 1 | 95.823 | 3.935 | 0 | 0 | 0 | 0 | 0 | 0.242 | 0 | 0 | 4.177 | 100 |

TABLE 22-continued

% main peak and % impurities for indacaterol liquid formulations stored at 5° C. for 5 weeks. Detection at 254 nm.

| Formulation | Timepoint (weeks) | Indacaterol (%) | RRT ~0.25 | RRT ~0.29 | RRT ~0.33 | RRT ~0.60 | RRT ~0.73 | RRT ~0.83 | RRT ~1.03 | RRT ~1.10 | RRT ~1.15 | Total Impurities | Total area |
|---|---|---|---|---|---|---|---|---|---|---|---|---|---|
| | 2 | 96.358 | 3.231 | 0 | 0.103 | 0.073 | 0 | 0 | 0.236 | 0 | 0 | 3.643 | 100.001 |
| | 3 | 96.827 | 2.745 | 0 | 0 | 0.143 | 0 | 0 | 0.284 | 0 | 0 | 3.172 | 99.999 |
| | 4 | 96.435 | 3.404 | 0 | 0 | 0 | 0 | 0 | 0.161 | 0 | 0 | 3.565 | 100 |
| | % change in 4 weeks | −0.482 | 0.596 | 0 | −0.027 | 0 | 0 | 0 | −0.087 | 0 | 0 | 0.482 | 0 |
| F5 | 0 | 97.189 | 2.546 | 0 | 0 | 0 | 0 | 0 | 0.265 | 0 | 0 | 2.811 | 100 |
| | 1 | 96.595 | 2.967 | 0 | 0.042 | 0.093 | 0.031 | 0 | 0.237 | 0 | 0 | 3.37 | 99.965 |
| | 2 | 96.999 | 2.601 | 0 | 0.046 | 0.077 | 0 | 0 | 0.243 | 0 | 0 | 2.967 | 99.966 |
| | 3 | 97.198 | 2.397 | 0 | 0.042 | 0.093 | 0.034 | 0 | 0.235 | 0 | 0 | 2.801 | 99.999 |
| | 4 | 97.006 | 2.724 | 0 | 0.007 | 0 | 0 | 0 | 0.264 | 0 | 0 | 2.995 | 100.001 |
| | % change in 4 weeks | −0.183 | 0.178 | 0 | 0.007 | 0 | 0 | 0 | −0.001 | 0 | 0 | 0.184 | 0.001 |
| F6 | 0 | 96.705 | 2.989 | 0 | 0 | 0 | 0 | 0 | 0.306 | 0 | 0 | 3.295 | 100 |
| | 1 | 95.733 | 3.898 | 0 | 0 | 0.116 | 0 | 0 | 0.252 | 0 | 0 | 4.266 | 99.999 |
| | 2 | 96.422 | 3.169 | 0 | 0.087 | 0.098 | 0 | 0 | 0.223 | 0 | 0 | 3.577 | 99.999 |
| | 3 | 96.867 | 2.702 | 0 | 0.084 | 0.121 | 0 | 0 | 0.226 | 0 | 0 | 3.133 | 100 |
| | 4 | 96.619 | 3.128 | 0 | 0 | 0 | 0 | 0 | 0.253 | 0 | 0 | 3.381 | 100 |
| | % change in 4 weeks | −0.086 | 0.139 | 0 | 0 | 0 | 0 | 0 | −0.053 | 0 | 0 | 0.086 | 0 |
| F7 | 0 | 98.477 | 0.095 | 0 | 0 | 0.052 | 0 | 0 | 0 | 1.216 | 0.121 | 1.484 | 99.961 |
| | 1 | 98.134 | 0.447 | 0 | 0 | 0.05 | 0 | 0 | 0 | 1.185 | 0.124 | 1.806 | 99.94 |
| | 2 | 98.123 | 0.43 | 0 | 0.009 | 0.048 | 0 | 0 | 0 | 1.198 | 0.123 | 1.808 | 99.931 |
| | 3 | 98.209 | 0.357 | 0 | 0.011 | 0.048 | 0 | 0 | 0 | 1.19 | 0.123 | 1.729 | 99.938 |
| | 4 | 98.477 | 0.132 | 0 | 0 | 0.049 | 0 | 0 | 0 | 1.2 | 0.124 | 1.505 | 99.982 |
| | % change in 4 weeks | 0.000 | 0.037 | 0 | 0 | −0.003 | 0 | 0 | 0 | −0.016 | 0.003 | 0.021 | 0.021 |
| F8 | 0 | 97.766 | 0.102 | 0 | 0.001 | 0.059 | 0.705 | 0 | 0 | 1.21 | 0.12 | 2.197 | 99.963 |
| | 1 | 97.443 | 0.443 | 0 | 0 | 0.045 | 0.703 | 0 | 0 | 1.179 | 0.122 | 2.492 | 99.935 |
| | 2 | 97.44 | 0.43 | 0 | 0.008 | 0.055 | 0.702 | 0 | 0 | 1.178 | 0.123 | 2.496 | 99.936 |
| | 3 | 97.514 | 0.352 | 0 | 0.009 | 0.05 | 0.7 | 0 | 0 | 1.196 | 0.124 | 2.431 | 99.945 |
| | 4 | 97.765 | 0.114 | 0 | 0.002 | 0.045 | 0.702 | 0 | 0 | 1.207 | 0.124 | 2.194 | 99.959 |
| | % change in 4 weeks | −0.001 | 0.012 | 0 | 0.001 | −0.014 | −0.003 | 0 | 0 | −0.003 | 0.004 | −0.003 | −0.004 |
| F9 | 0 | 97.777 | 0.109 | 0 | 0 | 0.05 | 0.71 | 0 | 0 | 1.202 | 0.118 | 2.189 | 99.966 |
| | 1 | 97.404 | 0.457 | 0 | 0 | 0.058 | 0.724 | 0 | 0 | 1.172 | 0.126 | 2.537 | 99.941 |
| | 2 | 97.439 | 0.432 | 0 | 0 | 0.051 | 0.715 | 0 | 0 | 1.187 | 0.124 | 2.518 | 99.957 |
| | 3 | 97.514 | 0.343 | 0 | 0 | 0.055 | 0.722 | 0 | 0 | 1.182 | 0.122 | 2.424 | 99.938 |
| | 4 | 97.749 | 0.136 | 0 | 0 | 0.049 | 0.71 | 0 | 0 | 1.195 | 0.121 | 2.211 | 99.96 |
| | % change in 4 weeks | −0.028 | 0.027 | 0 | 0 | −0.001 | 0 | 0 | 0 | −0.007 | 0.003 | 0.022 | −0.006 |

Example 9—Aerosol Performance Studies of Liquid Indacaterol Formulations

Aerosol performance studies of mono (indacaterol) and combo (indacaterol and glycopyrrolate) in solution formulations, delivered using various liquid inhalation devices, were performed using Laser Diffraction and Delivered Dose (DD) methods. For Laser diffraction, a specified volume of each formulation was placed into the test nebulizer reservoir and aerosolized to determine droplet size distribution (DSD). For Delivered Dose (DD), a breathing simulator, pre-set to a tidal breathing pattern (500 mL tidal volume, Inspiratory to Expiratory ratio (I:E) of 1:1, 15 BPM, sinusoidal waveform) as per USP<1601> (*United States Pharmacopeia*, section 1601), was used to draw inspiratory and expiratory airflow through the DD collection filter. The nebulizer, positioned as intended for use, was connected to the filter inlet, charged with drug product solution and nebulization initiated for the specified duration. The drug content was determined by RP-HPLC. Results are presented in Table 23, Table 24, and Figure X1. LC Sprint is an air-jet nebulizer. InnoSpire Go and FLYP are vibrating mesh nebulizers. The LC Sprint, InnoSpire Go, and FLYP nebulizers are not breath-actuated.

TABLE 23

Laser Diffraction testing of Liquid formulations of indacaterol for aerosol performance studies. Results are the mean (n = 3) with one standard deviation in brackets.

| Name Code | Composition | Device | Charge Volume (mL) | Nominal Dose (μg) | Volumetric Median Diameter (μm) | Grain Size Distribution (μm) | Fine Particle Fraction0 <5.0 μm (%) |
|---|---|---|---|---|---|---|---|
| G3 | 100 μg/mL indacaterol maleate in 200 | LC Sprint (Air-Jet) | 4.0 | 309 [1] | 5.2 | 1.9 | 47.9 |

TABLE 23-continued

Laser Diffraction testing of Liquid formulations of indacaterol for aerosol performance studies. Results are the mean (n = 3) with one standard deviation in brackets.

| Name Code | Composition | Device | Charge Volume (mL) | Nominal Dose (μg) | Volumetric Median Diameter (μm) | Grain Size Distribution (μm) | Fine Particle Fraction0 <5.0 μm (%) |
|---|---|---|---|---|---|---|---|
| | mM mannitol, 10 mM sodium chloride, 10 mM citrate buffer, pH 3.0 | | | | | | |
| G7 | 500 μg/mL indacaterol base in 200 mM mannitol, 10 mM sodium chloride, 10 mM citrate buffer, pH 3.0 | InnoSpire Go (ISG) | 0.60 | 300 | 4.4 (0.0) | 1.5 (0.0) | 59.2 (0.2) |
| | | | 0.80 | 400 | 4.3 (0.0) | 1.5 (0.0) | 59.8 (0.3) |
| | | | 1.30 | 650 | 4.3 (0.0) | 1.5 (0.0) | 59.8 (0.2) |
| | | FLYP | 0.60 | 300 | 5.5 (0.0) | 1.4 (0.0) | 43.3 (0.6) |
| | | | 0.80 | 400 | 5.3 (0.1) | 1.4 (0.0) | 45.7 (0.7) |
| | | | 1.30 | 650 | 5.2 (0.0) | 1.4 (0.0) | 47.7 (0.6) |
| | | VMN-1 with BA [2] | 0.10 | 50 | 4.7 (0.1) | 1.5 (0.0) | 54.8 (0.8) |
| | | | 0.20 | 100 | 4.7 (0.0) | 1.5 (0.0) | 54.6 (0.4) |
| | | | 0.27 | 135 | 0.0 (0.0) | 0.0 (0.0) | 54.6 (0.4) |
| | | | 0.45 | 225 | 4.6 (0.0) | 1.5 (0.0) | 55.5 (0.1) |
| | | VMN-2 with BA [3] | 0.37 | 185 | 4.6 (0.1) | 1.8 (0.1) | 55.1 (1.5) |
| G8 | 500 μg/mL indacaterol base and 350 μg/mL glycopyrrolate bromide in 200 mM mannitol, 10 mM sodium chloride, 10 mM citrate buffer, pH 3.0 | VMN-2 with BA [3] | 0.30 | 150 | 4.5 (0.1) | 1.7 (0.1) | 57.4 (2.1) |
| | | | 0.37 | 185 | 4.5 (0.1) | 1.7 (0.0) | 56.8 (1.9) |
| | | | 0.55 | 275 | 4.5 (0.1) | 1.7 (0.0) | 57.0 (2.2) |

[1] Indacaterol freebase.
[2] Investigated vibrating mesh nebulizer (VMN) with breath-actuated (BA) from a device company 1.
[3] Investigated vibrating mesh nebulizer (VMN) with breath-actuated (BA) from a device company 2.

TABLE 24

Delivered testing of Liquid formulations of indacaterol for aerosol performance studies.

| Name Code | Composition | Device | Charge Volume (mL) | Nominal Dose (μg) | DD Indacaterol (μg)[4] | DD Glycopyrrolate (μg) |
|---|---|---|---|---|---|---|
| G3 | 100 μg/mL indacaterol maleate in 200 mM mannitol, 10 mM sodium chloride, 10 mM citrate buffer, pH 3.0 | LC Sprint (Air-Jet) | 3.80 | 293 [1] | 72.7 | n/a |
| | | | 4.60 | 355 [1] | 93.7 | n/a |
| | | | 7.00 | 540 [1] | 136.3 | n/a |
| G7 | 500 μg/mL indacaterol base in 200 mM mannitol, 10 mM sodium chloride, 10 mM citrate buffer, pH 3.0 | InnoSpire Go (ISG) | 0.60 | 300 | 94.2 (2.1) | n/a |
| | | | 0.80 | 400 | 127.6 (4.8) | n/a |
| | | | 1.30 | 650 | 206.5 (3.1) | n/a |
| | | FLYP | 0.60 | 300 | 56.1 (9.2) | n/a |
| | | | 0.80 | 400 | 94.2 (19.7) | n/a |
| | | | 1.30 | 650 | 173.1 (27.1) | n/a |
| | | VMN-1 with BA [2] | 0.10 | 50 | 22.3 (0.5) | n/a |
| | | | 0.20 | 100 | 68.9 (5.8) | n/a |
| | | | 0.27 | 135 | 93.0 (5.4) | n/a |
| | | | 0.45 | 225 | 144.8 (8.4) | n/a |
| | | VMN-2 with BA [3] | 0.37 | 185 | 97.1 (10.8) | n/a |
| G8 | 500 μg/mL indacaterol base and 350 μg/mL glycolpyrrolate bromide in 200 mM mannitol, | VMN-2 with BA [3] | 0.30 | 150 | 72.0 (7.5) | TBD |
| | | | 0.37 | 185 | 99.1 (9.8) | TBD |
| | | | 0.55 | 275 | 178.5 (7.7) | TBD |

TABLE 24-continued

Delivered testing of Liquid formulations of indacaterol for aerosol performance studies.

10 mM sodium chloride, 10 mM citrate buffer, pH 3.0

| Name Code | DD (% nominal) | Treatment Time (minutes) | Liquid output rate (g/min) | Residual Mass (g) | Fine Particle Dose <5.0 μm (μg) |
|---|---|---|---|---|---|
| G3 | 28.3 | 5.93 | 0.45 | 1.20 | 34.8 |
|  | 30.2 | 7.73 | 0.41 | 1.48 | 44.9 |
|  | 28.8 | 11.53 | 0.45 | 1.94 | 65.3 |
| G7 | 31.4 (0.7) | 1.26 (0.06) | 0.41 (0.02) | 0.10 (0.01) | 55.7 (1.1) |
|  | 31.9 (1.2) | 1.78 (0.07) | 0.38 (0.02) | 0.12 (0.02) | 76.3 (3.5) |
|  | 31.8 (0.5) | 2.60 (0.03) | 0.44 (0.01) | 0.15 (0.04) | 123.4 (2.2) |
|  | 18.7 (3.1) | 1.53 (0.09) | 0.34 (0.09) | 0.07 (0.13) | 24.3 (4.3) |
|  | 23.5 (4.9) | 1.65 (0.13) | 0.47 (0.06) | 0.09 (0.02) | 43.1 (9.7) |
|  | 26.6 (4.2) | 3.27 (0.56) | 0.40 (0.02) | 0.09 (0.03) | 82.7 (14.0) |
|  | 44.5 (1.1) | 0.17 (0.00) | 0.38 (0.03) | 0.03 (0.01) | 12.3 (0.2) |
|  | 68.9 (5.8) | 0.50 (0.00) | 0.38 (0.01) | 0.02 (0.00) | 37.7 (3.1) |
|  | 68.9 (4.0) | 0.67 (0.00) | 0.37 (0.02) | 0.02 (0.00) | 50.8 (3.3) |
|  | 64.3 (3.7) | 1.00 (0.00) | 0.27 (0.22) | 0.19 (0.23) | 80.2 (4.7) |
|  | 53.7 (6.0) | 1.61 (0.7) | 0.18 (0.1) | 0.10 (0.0) | 53.6 (6.3) |
| G8 | 50.3 (5.2) | 1.61 (0.7) | 0.18 (0.1) | 0.10 (0.0) | 41.4 (5.2) |
|  | 56.1 (5.5) | 2.00 (0.5) | 0.15 (0.0) | 0.08 (0.0) | 56.4 (7.4) |
|  | 68.0 (2.9) | 3.93 (0.8) | 0.12 (0.0) | 0.09 (0.0) | 101.8 (8.0) |

[1] Indacaterol free base content in the indacaterol maleate.
[2] Investigated vibrating mesh nebulizer (VMN) with breath-actuated (BA) from a device company 1.
[3] Investigated vibrating mesh nebulizer (VMN) with breath-actuated (BA) from a device company 2.
[4] For $G^7$ and $G^8$, trials were run in triplicate. Measured data is an average of the three runs with the relative standard deviation given in brackets after the average value.

TBD = To be determined

Example 10—Liquid Indacaterol and Tiotropium Formulations

A series of formulations of indacaterol in combination with tiotropium were prepared for the stability study. Each formulation was initially prepared in a concentrated form and with a low pH to maximize the rate of indacaterol solubilization. Each formulation was transferred to a glass bottle, then indacaterol and tiotropium was added. The formulation in the bottles were stirred by magnetic stirrer until the indacaterol had solubilized. The pH of each formulation was measured and subsequently adjusted with 2 N NaOH and/or 2 N HCl to the target pH. The stirring were allowed to stir for another 30 minutes. The volume was made up to the target volume using water and the pH was checked to ensure target pH was maintained. Each formulation was filtered through a PVDF filter membrane to minimize particulate and microbial load and transferred to a biosafety cabinet (BSC) for vial filling. The osmolality and viscosity of the formulations were tested (see Table 25).

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention. All references in the present disclosure are incorporated herein.

We claim:

1. A method of treating a respiratory disorder, an inflammatory disorder of the airways and/or lungs, or an obstructive airway disease, the method comprising:
   delivering an aqueous pharmaceutical composition to the lungs of a patient in need thereof, wherein:
   the aqueous pharmaceutical composition comprises:
     from about 20 weight percent to about 99.9 weight percent water;
     indacaterol present at a concentration of about 10 μg/mL to about 600 μg/mL;

TABLE 25

Liquid formulations of indacaterol for stability studies.

| Name | Buffer (Citric Acid-Na Citrate) | pH | Excipients | Active Ingredient | Osmolality (mOsm/kg) | Viscosity (cP) |
|---|---|---|---|---|---|---|
| G10 | 10 mM | 3.0 | 200 mM mannitol 10 mM NaCl | 500 μg/mL indacaterol base 62.5 μg/mL tiotropium bromide monohydrate | 241.5 | 1.15 |
| G11 |  | 3.5 |  | 500 μg/mL indacaterol base 62.5 μg/mL tiotropium bromide monohydrate | 245.0 | 1.16 | glycopyrrolate, or a pharmaceutically acceptable salt thereof, present at a concentration of about 10 µg/mL to about 600 µg/mL;

two or more tonicity modifiers; and a buffer, wherein the indacaterol is present as a free base or as a pharmaceutical acceptable salt thereof without the presence of maleic acid from a maleate salt in the aqueous pharmaceutical composition, one of the two or more tonicity modifiers is present at a concentration from about 100 mM to about 500 mM, and the aqueous pharmaceutical composition is buffered to a pH from 2 to 6.

2. The method of claim 1, wherein the respiratory disorder, inflammatory disorder of the airways and/or lungs, or obstructive airway disease is chronic obstructive pulmonary disease (COPD).

3. A method of preparing the aqueous pharmaceutical composition of claim 1, the method comprising steps a) and b):
   a) adding the indacaterol and the glycopyrrolate, or a pharmaceutically acceptable salt thereof, to a liquid comprising water to form a mixture; and
   b) adjusting a pH of the mixture to obtain the aqueous pharmaceutical composition.

4. The method of claim 3, wherein step b) comprises adding an acid or an acid form of the buffer, wherein the acid or the acid form of the buffer is added until the water has a pH equal to or below 2.0.

5. The method of claim 1, wherein the respiratory disorder, the inflammatory disorder of the airways and/or lungs, or the obstructive airway disease is asthma.

6. The method of claim 1, wherein the aqueous pharmaceutical composition is administered to the lungs of the patient in need thereof at least once daily.

7. The method of claim 6, wherein the aqueous pharmaceutical composition is administered to the lungs of the patient in need thereof twice daily.

8. The method of claim 1, wherein the indacaterol is present at a concentration of about 50 µg/mL to about 200 µg/mL in the aqueous pharmaceutical composition.

9. The method of claim 1, wherein the water is present in an amount ranging from about 80 weight percent to about 99.9 weight percent in the aqueous pharmaceutical composition.

10. The method of claim 1, wherein the buffer comprises an anion selected from the group consisting of acetate, bromide, chloride, citrate, furoate, fumarate, propionate, succinate, sulfate, tartrate, and xinafoate.

11. The method of claim 10, wherein the anion of the buffer in the aqueous pharmaceutical composition is acetate.

12. The method of claim 11, wherein the buffer in the aqueous pharmaceutical composition is prepared from a combination of acetic acid and sodium hydroxide.

13. The method of claim 11, wherein the buffer in the aqueous pharmaceutical composition is prepared from a combination of acetic acid and sodium acetate.

14. The method of claim 10, wherein the anion of the buffer in the aqueous pharmaceutical composition is citrate.

15. The method of claim 14, wherein the buffer in the aqueous pharmaceutical composition is prepared from a combination of citric acid and trisodium citrate.

16. The method of claim 14, wherein the buffer in the aqueous pharmaceutical composition is prepared from a combination of citric acid and sodium hydroxide.

17. The method of claim 10, wherein the anion of the buffer in the aqueous pharmaceutical composition is tartrate.

18. The method of claim 1, wherein the aqueous pharmaceutical composition comprises a pH from 2 to 5.

19. The method of claim 1, wherein the aqueous pharmaceutical composition comprises a pH from 3 to 5.

20. The method of claim 1, wherein aqueous pharmaceutical composition further comprises tiotropium bromide.

21. The method of claim 1, wherein the glycopyrrolate, or a pharmaceutically acceptable salt thereof, is glycopyrronium bromide.

22. The method of claim 1, wherein the glycopyrrolate, or a pharmaceutically acceptable salt thereof, is present in the aqueous pharmaceutical composition at a concentration in a range from about 50 µg/mL to about 200 µg/mL.

23. The method of claim 1, wherein:
   the concentration of the indacaterol in the aqueous pharmaceutical composition is between about 50 µg/mL to about 200 µg/mL; and
   the concentration of the glycopyrrolate, or a pharmaceutically acceptable salt thereof, in the aqueous pharmaceutical composition is between about 50 µg/mL to about 200 µg/mL.

24. The method of claim 1, wherein the concentration of the indacaterol is greater than the concentration of the glycopyrrolate, or a pharmaceutically acceptable salt thereof, in the aqueous pharmaceutical composition.

25. The method of claim 1, wherein the aqueous pharmaceutical composition further comprises mometasone, or a pharmaceutically acceptable salt thereof.

26. The method of claim 1, wherein:
   the indacaterol is present in the aqueous pharmaceutical composition at a concentration of about 50 µg/mL to about 200 µg/mL; and
   the aqueous pharmaceutical composition is buffered to a pH from 2 to 5.

27. The method of claim 1, wherein:
   the water is present in the aqueous pharmaceutical composition in an amount ranging from about 80 weight percent to about 99.9 weight percent;
   the indacaterol is present in the aqueous pharmaceutical composition at a concentration of about 50 µg/mL to about 200 µg/mL; and
   the glycopyrrolate, or a pharmaceutically acceptable salt thereof, is present in the aqueous pharmaceutical composition at a concentration of about 50 µg/mL to about 200 µg/mL.

28. The method of claim 1, wherein the aqueous pharmaceutical composition is suitable for delivery to lungs of a patient in need thereof using a device.

29. The method of claim 28, further comprising administering an inhaled corticosteroid to the lungs of the patient in need thereof using the device.

30. The method of claim 3, wherein step b) comprises waiting for a time period until the mixture reaches an equilibrium.

31. The method of claim 30, wherein the time period is between about 12 hours to about 72 hours.

32. The method of claim 4, wherein the buffer comprises an anion selected from the group consisting of acetate, bromide, chloride, citrate, furoate, fumarate, propionate, succinate, sulfate, tartrate, and xinafoate.

33. The method of claim 32, wherein the anion of the buffer is selected from the group consisting of acetate, citrate, and tartrate.

34. A device for delivering the aqueous pharmaceutical composition of claim 1 and an inhaled corticosteroid to lungs of a patient in need thereof.

35. The method of claim 1, wherein the method further comprises aerosolizing the aqueous pharmaceutical composition via a jet nebulizer.

36. The method of claim 1, wherein the method further comprises aerosolizing the aqueous pharmaceutical composition via a vibrating mesh nebulizer.

37. The method of claim 1, wherein the one of the two or more tonicity modifiers is present at a concentration from about 100 mM to about 200 mM.

38. The method of claim 1, wherein the two or more tonicity modifiers comprises sodium chloride.

39. The method of claim 38, wherein sodium chloride is present at about 10 mM.

* * * * *